(12) United States Patent
Maxik et al.

(10) Patent No.: US 9,265,968 B2
(45) Date of Patent: Feb. 23, 2016

(54) SYSTEM FOR GENERATING NON-HOMOGENOUS BIOLOGICALLY-ADJUSTED LIGHT AND ASSOCIATED METHODS

(71) Applicant: Biological Illumination, LLC, Satellite Beach, FL (US)

(72) Inventors: Fredric S. Maxik, Cocoa Beach, FL (US); David E. Bartine, Cocoa, FL (US); Robert R. Soler, Cocoa Beach, FL (US); Valerie A. Bastien, Melbourne, FL (US); James Lynn Schellack, Skiatook, OK (US)

(73) Assignee: Biological Illumination, LLC, Melbourne, FL (US)

( * ) Notice: Subject to any disclaimer, the term of this patent is extended or adjusted under 35 U.S.C. 154(b) by 29 days.

(21) Appl. No.: 14/260,371

(22) Filed: Apr. 24, 2014

(65) Prior Publication Data
US 2014/0236266 A1    Aug. 21, 2014

Related U.S. Application Data

(63) Continuation of application No. 13/803,825, filed on Mar. 14, 2013, now Pat. No. 8,743,023, which is a
(Continued)

(51) Int. Cl.
*G09G 3/14* (2006.01)
*G09G 3/16* (2006.01)
(Continued)

(52) U.S. Cl.
CPC .............. *A61N 5/0618* (2013.01); *H05B 37/02* (2013.01); *H05B 37/029* (2013.01); *A61N 2005/0626* (2013.01); *A61N 2005/0652* (2013.01); *A61N 2005/0663* (2013.01)

(58) Field of Classification Search
USPC ........... 315/291, 294, 297, 151, 82, 154–159, 315/307; 455/39; 398/34, 79, 90–95, 98, 398/196–197; 345/426, 428, 589, 204, 207, 345/211, 214, 690–691, 22, 45–46, 48, 345/63–64, 76–77, 84; 340/870.17, 870.18, 340/870.25, 870.26, 815.75
See application file for complete search history.

(56) References Cited

U.S. PATENT DOCUMENTS

| 5,046,494 A | 9/1991 | Searfoss et al. |
|---|---|---|
| 5,523,878 A | 6/1996 | Wallace et al. |

(Continued)

FOREIGN PATENT DOCUMENTS

| CN | 101702421 A | 5/2010 |
|---|---|---|
| EP | 0851260 | 7/1998 |

(Continued)

OTHER PUBLICATIONS

U.S. Appl. No. 13/837,643, filed Mar. 2013, Fredric S. Maxik et al.
(Continued)

*Primary Examiner* — Wesner Sajous
(74) *Attorney, Agent, or Firm* — Mark Malek; Daniel Pierron; Wilderman Malek, PL

(57) ABSTRACT

A lighting apparatus including a plurality of luminaires, each including a controller configured to operate the luminaire and positioned in communication with a computerized device. Each luminaire is selectively operable to emit source light, characterized by a dominant source light wavelength within a range from 390 nanometers to 750 nanometers. The luminaires are arrangeable so as to form an array. Some luminaires of the plurality of luminaires are operable such that at least two of the luminaires emit source lights with different dominant source light wavelengths and the source lights emitted by the luminaires combine to form a combined light at a distance from the luminaires defined as a combining distance. The dominant source light wavelength of some of the luminaires varies with time. The luminaires are configured to be operated to selectively emit light having a spectral power distribution that reduces melatonin suppression.

24 Claims, 9 Drawing Sheets

Related U.S. Application Data continuation-in-part of application No. 13/709,942, filed on Dec. 10, 2012, now Pat. No. 7,760,370, and a continuation-in-part of application No. 13/107,928, filed on May 15, 2011, now Pat. No. 8,547,391, and a continuation-in-part of application No. 13/234,371, filed on Sep. 16, 2011, now Pat. No. 8,465,167, and a continuation-in-part of application No. 13/652,207, filed on Oct. 15, 2012, now Pat. No. 8,643,276, which is a continuation of application No. 13/174,339, filed on Jun. 30, 2011, now Pat. No. 8,324,808, which is a continuation-in-part of application No. 12/842,887, filed on Jul. 23, 2010, now Pat. No. 8,253,336.

(60) Provisional application No. 61/643,308, filed on May 6, 2012, provisional application No. 61/643,316, filed on May 6, 2012.

(51) Int. Cl.
*G09G 3/30* (2006.01)
*G09G 5/02* (2006.01)
*G09G 5/10* (2006.01)
*H04J 14/02* (2006.01)
*A61N 5/06* (2006.01)
*H05B 37/02* (2006.01)

(56) References Cited

U.S. PATENT DOCUMENTS

| | | | |
|---|---|---|---|
| 5,680,230 A | 10/1997 | Kaburagi et al. |
| 5,704,701 A | 1/1998 | Kavanagh et al. |
| 5,813,753 A | 9/1998 | Vriens et al. |
| 5,997,150 A | 12/1999 | Anderson |
| 6,140,646 A | 10/2000 | Busta et al. |
| 6,259,572 B1 | 7/2001 | Meyer, Jr. |
| 6,341,876 B1 | 1/2002 | Moss et al. |
| 6,356,700 B1 | 3/2002 | Strobl |
| 6,450,652 B1 | 9/2002 | Karpen |
| 6,459,919 B1 | 10/2002 | Lys et al. |
| 6,528,954 B1 | 3/2003 | Lys et al. |
| 6,561,656 B1 | 5/2003 | Kojima et al. |
| 6,577,080 B2 | 6/2003 | Lys et al. |
| 6,586,882 B1 | 7/2003 | Harbers |
| 6,594,090 B2 | 7/2003 | Kruschwitz et al. |
| 6,733,135 B2 | 5/2004 | Dho |
| 6,734,639 B2 | 5/2004 | Chang et al. |
| 6,762,562 B2 | 7/2004 | Leong |
| 6,767,111 B1 | 7/2004 | Lai |
| 6,817,735 B2 | 11/2004 | Shimizu et al. |
| 6,870,523 B1 | 3/2005 | Ben-David et al. |
| 6,871,982 B2 | 3/2005 | Holman et al. |
| 6,902,296 B2 | 6/2005 | Searfoss, III |
| 6,967,761 B2 | 11/2005 | Starkweather et al. |
| 6,974,713 B2 | 12/2005 | Patel et al. |
| 7,008,559 B2 | 3/2006 | Chen |
| 7,012,542 B2 | 3/2006 | Powell et al. |
| 7,034,934 B2 | 4/2006 | Manning |
| 7,042,623 B1 | 5/2006 | Huibers et al. |
| 7,058,197 B1 | 6/2006 | McGuire et al. |
| 7,070,281 B2 | 7/2006 | Kato |
| 7,072,096 B2 | 7/2006 | Holman et al. |
| 7,075,707 B1 | 7/2006 | Rapaport et al. |
| 7,083,304 B2 | 8/2006 | Rhoads |
| 7,095,053 B2 | 8/2006 | Mazzochette et al. |
| 7,112,806 B2 | 9/2006 | Lussier |
| 7,140,752 B2 | 11/2006 | Ashdown |
| 7,144,131 B2 | 12/2006 | Rains |
| 7,157,745 B2 | 1/2007 | Blonder et al. |
| 7,178,941 B2 | 2/2007 | Roberge et al. |
| 7,184,201 B2 | 2/2007 | Duncan |
| 7,187,484 B2 | 3/2007 | Mehrl |
| 7,213,926 B2 | 5/2007 | May et al. |
| 7,234,844 B2 | 6/2007 | Bolta et al. |
| 7,246,923 B2 | 7/2007 | Conner |
| 7,247,874 B2 | 7/2007 | Bode et al. |
| 7,252,408 B2 | 8/2007 | Mazzochette et al. |
| 7,255,469 B2 | 8/2007 | Wheatley et al. |
| 7,261,453 B2 | 8/2007 | Morejon et al. |
| 7,289,090 B2 | 10/2007 | Morgan |
| 7,300,177 B2 | 11/2007 | Conner |
| 7,303,291 B2 | 12/2007 | Ikeda et al. |
| 7,319,293 B2 | 1/2008 | Maxik |
| 7,319,298 B2 | 1/2008 | Jungwirth et al. |
| 7,324,076 B2 | 1/2008 | Lee et al. |
| 7,325,956 B2 | 2/2008 | Morejon et al. |
| 7,342,658 B2 | 3/2008 | Kowarz et al. |
| 7,344,279 B2 | 3/2008 | Mueller et al. |
| 7,349,095 B2 | 3/2008 | Kurosaki |
| 7,353,859 B2 | 4/2008 | Stevanovic et al. |
| 7,369,056 B2 | 5/2008 | McCollough et al. |
| 7,382,091 B2 | 6/2008 | Chen |
| 7,382,632 B2 | 6/2008 | Alo et al. |
| 7,400,439 B2 | 7/2008 | Holman |
| 7,427,146 B2 | 9/2008 | Conner |
| 7,429,983 B2 | 9/2008 | Islam |
| 7,434,946 B2 | 10/2008 | Huibers |
| 7,436,996 B2 | 10/2008 | Ben-Chorin |
| 7,438,443 B2 | 10/2008 | Tatsuno et al. |
| 7,476,016 B2 | 1/2009 | Kurihara |
| 7,497,596 B2 | 3/2009 | Ge |
| 7,520,607 B2 | 4/2009 | Casper et al. |
| 7,520,642 B2 | 4/2009 | Holman et al. |
| 7,521,875 B2 | 4/2009 | Maxik |
| 7,528,421 B2 | 5/2009 | Mazzochette |
| 7,530,708 B2 | 5/2009 | Park |
| 7,537,347 B2 | 5/2009 | Dewald |
| 7,540,616 B2 | 6/2009 | Conner |
| 7,556,376 B2 | 7/2009 | Ishak et al. |
| 7,556,406 B2 | 7/2009 | Petroski et al. |
| 7,573,210 B2 | 8/2009 | Ashdown et al. |
| 7,598,686 B2 | 10/2009 | Lys et al. |
| 7,598,961 B2 | 10/2009 | Higgins |
| 7,605,971 B2 | 10/2009 | Ishii et al. |
| 7,619,372 B2 | 11/2009 | Garrity |
| 7,626,755 B2 | 12/2009 | Furuya et al. |
| 7,633,093 B2 | 12/2009 | Blonder et al. |
| 7,633,779 B2 | 12/2009 | Garrity et al. |
| 7,637,643 B2 | 12/2009 | Maxik |
| 7,677,736 B2 | 3/2010 | Kasazumi et al. |
| 7,678,140 B2 | 3/2010 | Brainard et al. |
| 7,679,281 B2 | 3/2010 | Kim et al. |
| 7,684,007 B2 | 3/2010 | Hull et al. |
| 7,687,753 B2 | 3/2010 | Ashdown |
| 7,703,943 B2 | 4/2010 | Li et al. |
| 7,705,810 B2 | 4/2010 | Choi et al. |
| 7,708,452 B2 | 5/2010 | Maxik et al. |
| 7,709,811 B2 | 5/2010 | Conner |
| 7,719,766 B2 | 5/2010 | Grasser et al. |
| 7,728,846 B2 | 6/2010 | Higgins et al. |
| 7,732,825 B2 | 6/2010 | Kim et al. |
| 7,748,845 B2 | 7/2010 | Casper et al. |
| 7,766,490 B2 | 8/2010 | Harbers et al. |
| 7,819,556 B2 | 10/2010 | Heffington et al. |
| 7,828,453 B2 | 11/2010 | Tran et al. |
| 7,828,465 B2 | 11/2010 | Roberge et al. |
| 7,832,878 B2 | 11/2010 | Brukilacchio et al. |
| 7,834,867 B2 | 11/2010 | Sprague et al. |
| 7,835,056 B2 | 11/2010 | Doucet et al. |
| 7,841,714 B2 | 11/2010 | Grueber |
| 7,845,823 B2 | 12/2010 | Mueller et al. |
| 7,855,376 B2 | 12/2010 | Cantin et al. |
| 7,871,839 B2 | 1/2011 | Lee |
| 7,880,400 B2 | 2/2011 | Zhou et al. |
| 7,889,430 B2 | 2/2011 | El-Ghoroury et al. |
| 7,906,789 B2 | 3/2011 | Jung et al. |
| 7,928,565 B2 | 4/2011 | Brunschwiler et al. |
| 7,972,030 B2 | 7/2011 | Li |
| 7,976,182 B2 | 7/2011 | Ribarich |
| 7,976,205 B2 | 7/2011 | Grotsch et al. |
| 7,984,989 B2 | 7/2011 | Gruber |
| 8,016,443 B2 | 9/2011 | Falicoff et al. |
| 8,040,070 B2 | 10/2011 | Myers et al. |

(56) References Cited

U.S. PATENT DOCUMENTS

| | | | |
|---|---|---|---|
| 8,047,660 B2 | 11/2011 | Penn et al. | |
| 8,049,763 B2 | 11/2011 | Kwak et al. | |
| 8,061,857 B2 | 11/2011 | Liu et al. | |
| 8,070,302 B2 | 12/2011 | Hatanaka et al. | |
| 8,076,680 B2 | 12/2011 | Lee et al. | |
| 8,083,364 B2 | 12/2011 | Allen | |
| 8,096,668 B2 | 1/2012 | Abu-Ageel | |
| 8,115,419 B2 | 2/2012 | Given et al. | |
| 8,164,844 B2 | 4/2012 | Toda et al. | |
| 8,182,106 B2 | 5/2012 | Shin et al. | |
| 8,182,115 B2 | 5/2012 | Takahashi et al. | |
| 8,188,687 B2 | 5/2012 | Lee et al. | |
| 8,192,047 B2 | 6/2012 | Bailey et al. | |
| 8,207,676 B2 | 6/2012 | Hilgers | |
| 8,212,836 B2 | 7/2012 | Matsumoto et al. | |
| 8,243,278 B2 | 8/2012 | Valois et al. | |
| 8,253,336 B2 | 8/2012 | Maxik et al. | |
| 8,255,487 B2 | 8/2012 | Valois et al. | |
| 8,256,921 B2 | 9/2012 | Crookham et al. | |
| 8,264,172 B2 | 9/2012 | Valois et al. | |
| 8,274,089 B2 | 9/2012 | Lee | |
| 8,297,783 B2 | 10/2012 | Kim | |
| 8,304,978 B2 | 11/2012 | Kim et al. | |
| 8,310,171 B2 | 11/2012 | Reisenauer et al. | |
| 8,319,445 B2 | 11/2012 | McKinney et al. | |
| 8,324,808 B2 | 12/2012 | Maxik et al. | |
| 8,324,823 B2 | 12/2012 | Choi et al. | |
| 8,324,840 B2 | 12/2012 | Shteynberg et al. | |
| 8,331,099 B2 | 12/2012 | Geissler et al. | |
| 8,337,029 B2 | 12/2012 | Li | |
| 8,378,574 B2 | 2/2013 | Schlangen et al. | |
| 8,384,984 B2 | 2/2013 | Maxik et al. | |
| 8,401,231 B2 | 3/2013 | Maxik et al. | |
| 8,405,299 B2 | 3/2013 | Toda et al. | |
| 8,410,717 B2 | 4/2013 | Shteynberg et al. | |
| 8,410,725 B2 | 4/2013 | Jacobs et al. | |
| 8,427,311 B2 | 4/2013 | Schlangen | |
| 8,427,590 B2 | 4/2013 | Raring et al. | |
| 8,441,210 B2 | 5/2013 | Shteynberg et al. | |
| 8,441,214 B2 | 5/2013 | Anderson | |
| 8,446,095 B2 | 5/2013 | Maxik et al. | |
| 8,465,167 B2 | 6/2013 | Maxik et al. | |
| 8,492,995 B2 | 7/2013 | Maxik et al. | |
| 8,531,126 B2 | 9/2013 | Kaihotsu et al. | |
| 8,547,391 B2 | 10/2013 | Maxik et al. | |
| 8,643,276 B2 | 2/2014 | Maxik et al. | |
| 8,662,672 B2 | 3/2014 | Hikmet et al. | |
| 8,674,613 B2 | 3/2014 | Gray et al. | |
| 8,678,787 B2 | 3/2014 | Hirata et al. | |
| 8,680,457 B2 | 3/2014 | Maxik et al. | |
| 8,686,641 B2 | 4/2014 | Maxik et al. | |
| 8,733,949 B2 | 5/2014 | Chong et al. | |
| 8,743,023 B2 | 6/2014 | Maxik et al. | |
| 8,754,832 B2 | 6/2014 | Maxik et al. | |
| 8,760,370 B2 | 6/2014 | Maxik et al. | |
| 8,761,447 B2 | 6/2014 | Maxik et al. | |
| 8,770,773 B2 | 7/2014 | Yoshida et al. | |
| 8,770,821 B2 | 7/2014 | Ijzerman et al. | |
| 2002/0113555 A1 | 8/2002 | Lys et al. | |
| 2004/0052076 A1 | 3/2004 | Mueller et al. | |
| 2004/0093045 A1 | 5/2004 | Bolta | |
| 2004/0119086 A1 | 6/2004 | Yano et al. | |
| 2005/0062446 A1* | 3/2005 | Ashdown | 315/324 |
| 2005/0189557 A1 | 9/2005 | Mazzochette et al. | |
| 2005/0218780 A1 | 10/2005 | Chen | |
| 2005/0267213 A1 | 12/2005 | Gold et al. | |
| 2006/0002108 A1 | 1/2006 | Ouderkirk et al. | |
| 2006/0002110 A1 | 1/2006 | Dowling et al. | |
| 2006/0164005 A1 | 7/2006 | Sun | |
| 2006/0285193 A1 | 12/2006 | Kimura et al. | |
| 2007/0013871 A1 | 1/2007 | Marshall et al. | |
| 2007/0159492 A1 | 7/2007 | Lo et al. | |
| 2007/0165193 A1 | 7/2007 | Kubo et al. | |
| 2007/0262714 A1 | 11/2007 | Bylsma | |
| 2008/0119912 A1 | 5/2008 | Hayes | |
| 2008/0143973 A1 | 6/2008 | Wu | |
| 2008/0198572 A1 | 8/2008 | Medendorp | |
| 2008/0224024 A1* | 9/2008 | Ashdown | 250/205 |
| 2008/0232084 A1 | 9/2008 | Kon | |
| 2009/0059585 A1 | 3/2009 | Chen et al. | |
| 2009/0128781 A1 | 5/2009 | Li | |
| 2009/0273931 A1 | 11/2009 | Ito et al. | |
| 2009/0284169 A1* | 11/2009 | Valois | 315/291 |
| 2009/0284747 A1* | 11/2009 | Valois | 356/448 |
| 2009/0303694 A1 | 12/2009 | Roth et al. | |
| 2010/0001652 A1 | 1/2010 | Damsleth | |
| 2010/0006762 A1 | 1/2010 | Yoshida et al. | |
| 2010/0051976 A1 | 3/2010 | Rooymans | |
| 2010/0076250 A1 | 3/2010 | Van Woudenberg | |
| 2010/0084992 A1* | 4/2010 | Valois et al. | 315/291 |
| 2010/0103389 A1 | 4/2010 | McVea et al. | |
| 2010/0111369 A1 | 5/2010 | Lussier | |
| 2010/0121420 A1 | 5/2010 | Fiset et al. | |
| 2010/0202129 A1 | 8/2010 | Abu-Ageel | |
| 2010/0244735 A1 | 9/2010 | Buelow, II | |
| 2010/0244740 A1 | 9/2010 | Alpert et al. | |
| 2010/0270942 A1 | 10/2010 | Hui et al. | |
| 2010/0277084 A1 | 11/2010 | Lee et al. | |
| 2010/0321641 A1 | 12/2010 | Van Der Lubbe | |
| 2011/0012137 A1 | 1/2011 | Lin et al. | |
| 2011/0080635 A1 | 4/2011 | Takeuchi | |
| 2011/0310446 A1 | 12/2011 | Komatsu | |
| 2012/0008326 A1 | 1/2012 | Jou | |
| 2012/0249013 A1* | 10/2012 | Valois et al. | 315/291 |
| 2012/0280625 A1* | 11/2012 | Zampini et al. | 315/151 |
| 2012/0285667 A1 | 11/2012 | Maxik et al. | |
| 2013/0088155 A1* | 4/2013 | Maxik et al. | 315/153 |
| 2013/0120963 A1* | 5/2013 | Holland et al. | 362/84 |
| 2013/0223055 A1* | 8/2013 | Holland et al. | 362/218 |
| 2013/0257312 A1* | 10/2013 | Maxik et al. | 315/297 |
| 2013/0293150 A1 | 11/2013 | Maxik et al. | |
| 2013/0293158 A1 | 11/2013 | Maxik et al. | |
| 2014/0015438 A1 | 1/2014 | Maxik et al. | |
| 2014/0107735 A1 | 4/2014 | Maxik et al. | |

FOREIGN PATENT DOCUMENTS

| | | |
|---|---|---|
| EP | 1671059 B1 | 4/2007 |
| EP | 2 199 657 | 6/2010 |
| EP | 2292464 A1 | 9/2011 |
| JP | 2008226567 | 9/2008 |
| WO | WO03098977 | 11/2003 |
| WO | WO2004011846 A1 | 2/2004 |
| WO | WO2006001221 A1 | 1/2006 |
| WO | WO2009121539 A1 | 10/2009 |
| WO | WO2012012245 A2 | 1/2012 |
| WO | WO2012064470 | 5/2012 |
| WO | WO2012135173 | 10/2012 |
| WO | WO2012158665 | 11/2012 |
| WO | 2012067916 | 12/2012 |

OTHER PUBLICATIONS

U.S. Appl. No. 13/842,875, filed Mar. 2013, Eric Holland et al.

Akashi, Yukio, et al., ""Assessment of Headlamp Glare and Potential Countermeasures: Survey of Advanced Front Lighting System (AFS), U.S. Department of Transportation, National Highway Traffic Safety Administration, Contract No. DTNH22-99-D-07005, (Dec. 2005).

Arthur P. Fraas, Heat Exchanger Design, 1989, p. 60, John Wiley & Sons, Inc., Canada.

Binnie et al. (1979) "Fluorescent Lighting and Epilepsy" Epilepsia 20(6):725-727.

Boeing, (Jul. 6, 2011), International Space Program, S684-13489 Revision A "ISS Interior Solid State Lighting Assembly (SSLA) Specification", Submitted to National Aeronautics and Space Administration, Johnson Space Center, Contract No. NAS15-10000, pp. 1-60.

Brainard, et al., (Aug. 15, 2001), "Action Spectrum for Melatonin Regulation in Humans: Evidence for a Novel Circadian Photoreceptor", The Journal of Neuroscience, 21(16):6405-6412.

(56) References Cited

OTHER PUBLICATIONS

Bullough, John, et al., "Discomfort Glare from Headlamps: Interactions Among Spectrum, Control of Gaze and Background Light Level", Society of Automotive Engineers, Inc., 2003-01-0296, (2003).
Charamisinau et al. (2005) "Semiconductor laser insert with Uniform Illumination for Use in Photodynamic Therapy" Appl Opt 44(24):5055-5068.
Derlofske, et al., "Headlamp Parameters and Glare", Society of Automotive Engineers, Inc., 2004-01-1280, (2004).
ERBA Shedding Light on Photosensitivity, One of Epilepsy's Most Complex Conditions. Photosensitivity and Epilepsy. Epilepsy Foundation. Accessed: Aug. 28, 2009. http://www.epilepsyfoundation.orgiaboutepilepsy/seizures/photosensitivity-/gerba.cfm.
Figueiro et al. (2004) "Spectral Sensitivity of the Circadian System" Proc. SPIE 5187:207.
Figueiro et al. (2008) "Retinal Mechanisms Determine the Subadditive Response to Polychromatic Light by the Human Circadian System" Neurosci Lett 438(2):242.
Gabrecht et al. (2007) "Design of a Light Delivery System for the Photodynamic Treatment of the Crohn's Disease" Proc. SPIE 6632:1-9.
H. A El-Shaikh, S. V. Garimella, "Enhancement of Air Jet Impingement Heat Transfer using Pin-Fin Heat Sinks", D IEEE Transactions on Components and Packaging Technology, Jun. 2000, vol. 23, No. 2.
Happawana et al. (2009) "Direct De-Ionized Water-Cooled Semiconductor Laser Package for Photodynamic Therapy of Esophageal Carcinoma: Design and Analysis" J Electron Pack 131(2):1-7.
Harding & Harding (1999) "Televised Material and Photosensitive Epilepsy" Epilepsia 40(Suppl. 4):65.
Hickcox, Sweater K., et al., Lighting Research Center, "Effect of different colored background lighting on LED discomfort glare perception", Proc. of SPIE, vol. 8484, 84840O-1, (2012).
Jones, Eric D., Light Emitting Diodes (LEDS) for General Lumination, an Optoelectronics Industry Development Association (OIDA) Technology Roadmap, OIDA Report, Mar. 2001, published by OIDA in Washington D.C.
J. Y. San, C. H. Huang, M. H, Shu, "Impingement cooling of a confined circular air jet", In t. J. Heat Mass Transf., 1997. pp. 1355-1364, vol. 40.
Kooi, Frank, "Yellow Lessens Discomfort Glare: Physiological Mechanism(S)", TNO Human Factors, Netherlands, Contract No. FA8655-03-1-3043, (Mar. 9, 2004).
Kuller & Laike (1998) "The Impact of Flicker from Fluorescent Lighting on Well-Being, Perfiormance and Physiological Arousal" Ergonomics 41(4):433-447.
Lakatos (2006) "Recent trends in the epidemiology of Inflammatory Bowel Disease: Up or Down?" World J Gastroenterol 12(38):6102.
Mace, Douglas, et al., "Countermeasures for Reducing the Effects of Headlight Glare", The Last Resource, Prepared for the AAA Foundation for Traffic Safety, pp. 1 to 110, (Dec. 2001).
Mehta, Arpit, "Map Colors of a CIE Plot and Color Temperature Using an RGB Color Sensor", Strategic Applications Engineer, Maxim Integrated Products, A1026, p. 1-11, (2005).
N. T. Obot, W. J. Douglas, A S. Mujumdar, "Effect of Semi-confinement on Impingement Heat Transfer", Proc. 7th Int. Heat Transf. Conf., 1982, pp. 1355-1364. vol. 3.
Ortner & Dorta (2006) "Technology Insight: Photodynamic Therapy for Cholangiocarcinoma" Nat Clin Pract Gastroenterol Hepatol 3(8):459-467.
Rea (2010) "Circadian Light" J Circadian Rhythms 8(1):2.
Rea et al. (2010) "The Potential of Outdoor Lighting for Stimulating the Human Circadian System" Alliance for Solid-State Illumination Systems and Technologies (ASSIST), May 13, 2010, p. 1-11.
Rosco Laboratories Poster "Color Filter Technical Data Sheet: #87 Pale Yellow Green" (2001).
Sivak, Michael, et al., "Blue Content of LED Headlamps and Discomfort Glare", The University of Michigan Transportation Research Institute, Report No. UMTRI-2005-2, pp. 1-18, (Feb. 2005).
S. A Solovitz, L. D. Stevanovic, R. A Beaupre, "Microchannels Take Heatsinks to the Next Level", Power Electronics Technology, Nov. 2006.
Stevens (1987) "Electronic Power Use and Breast Cancer: A Hypothesis" Am J Epidemiol 125(4):556-561.
Stockman, Andrew, "The spectral sensitivity of the human short-wavelength sensitive cones derived from thresholds and color matches", Pergamon, Vision Research 39, pages, 2901-2927 (1999).
Tannith Cattermole, "Smart Energy Class controls light on demand", Gizmag.com, Apr. 18, 2010 accessed Nov. 1, 2011.
Topalkara et al. (1998) "Effects of flash frequency and repetition of intermittent photic stimulation on photoparoxysmal responses" Seizure 7(13):249-253.
Veitch & McColl (1995) "Modulation of Fluorescent Light: Flicker Rate and Light Source Effects on Visual Performance and Visual Comfort" Lighting Research and Technology 27:243-256.
Wang (2005) "The Critical Role of Light in Promoting Intestinal Inflammation and Crohn's Disease" J Immunol 174 (12):8173-8182.
Wilkins et al. (1979) "Neurophysical aspects of pattern-sensitive epilepsy" Brain 102:1-25.
Wilkins et al. (1989) "Fluorescent lighting, headaches, and eyestrain" Lighting Res Technol 21(1):11-18.
Yongmann M. Chung, Kai H. Luo, "Unsteady Heat Transfer Analysis of an Impinging Jet", Journal of Heat Transfer—Transactions of the ASME, Dec. 2002, pp. 1039-1048, vol. 124, No. 6.
Office Action dated Oct. 24, 2014, for related U.S. Appl. No. 13/832,459, filed Mar. 15, 2013 (26 pages).

\* cited by examiner

SYSTEM FOR GENERATING NON-HOMOGENOUS BIOLOGICALLY-ADJUSTED LIGHT AND ASSOCIATED METHODS

RELATED APPLICATIONS

This application is a continuation and claims the benefit under 35 U.S.C. §120 of U.S. patent application Ser. No. 13/803,825 titled System for Generating Non-Homogenous Biologically-Adjusted Light and Associated Methods filed Mar. 14, 2013, which is in turn a continuation-in-part of U.S. patent application Ser. No. 13/709,942 titled System for Generating Non-Homogenous Light and Associated Methods filed Dec. 10, 2012, which in turn claimed the benefit under 35 U.S.C. §119(e) of U.S. Provisional Patent Application Ser. No. 61/643,308 titled Tunable Light System and Associated Methods filed May 6, 2012, and U.S. Provisional Patent Application Ser. No. 61/643,316 titled Luminaire Having an Adaptable Light Source and Associated Methods filed May 6, 2012. Furthermore, application Ser. No. 13/803,825 was also a continuation-in-part of U.S. patent application Ser. No. 13/107,928 titled High Efficacy Lighting Signal Converter and Associated Methods filed May 15, 2011, now U.S. Pat. No. 8,547,391, and U.S. patent application Ser. No. 13/234,371 titled Color Conversion Occlusion and Associated Methods filed Sep. 16, 2011, now U.S. Pat. No. 8,465,167. Additionally, application Ser. No. 13/803,825 was also a continuation-in-part of U.S. patent application Ser. No. 13/652,207 titled LED Lamp for Producing Biologically-Corrected Light filed Oct. 15, 2012, now U.S. Pat. No. 8,643,276, which is in turn a continuation of U.S. patent application Ser. No. 13/174,339 titled LED Lamp for Producing Biologically-Corrected Light filed Jun. 30, 2011, now U.S. Pat. No. 8,324,808, which is in turn a continuation-in-part of U.S. patent application Ser. No. 12/842,887 titled LED Lamp for Producing Biologically-Corrected Light filed Jul. 23, 2010, now U.S. Pat. No. 8,253,336. The contents of all of the above-referenced patents and applications are incorporated by reference herein in their entireties, except to the extent disclosures therein are inconsistent with disclosures herein.

FIELD OF THE INVENTION

The present invention relates to systems and methods for producing light and, more specifically, systems and methods for producing light that combines to form light having desirable characteristics.

BACKGROUND OF THE INVENTION

Lighting devices intended to provide illumination for a room have tended to operate according to one of two principles; to provide light that is desirable for everyday use, or light that is desirable for entertainment value. Light intended for the former has been static, consistently producing light of a given color, color temperature, or brightness, although so-called dimmer lights, which change the brightness of the light, are known. Light intended for the latter tends to be colored, hence usually having a lower color rendering index (CRI), and has also tended to be dimmer, which tends to make such light generally unsuitable for normal lighting purposes. Therefore, there is a need for a lighting device that can simultaneously produce light that is dynamic and entertaining while also being suitable for normal lighting purposes.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the foregoing in mind, embodiments of the present invention are related to a lighting apparatus comprising a plurality of luminaires, where each luminaire may comprise a controller configured to operate the luminaire and positioned in communication with a computerized device. Additionally, each luminaire may be selectively operable to emit source light, the source light is characterized by a dominant source light wavelength within a range from about 390 nanometers to about 750 nanometers. Furthermore, the plurality of luminaires may be arrangeable so as to form an array.

In some embodiments, at least some luminaires of the plurality of luminaires are operable such that at least two of the plurality of luminaires emit source lights with different dominant source light wavelengths, and such that the one or more source lights emitted by the plurality of luminaires combine to form a combined light at a distance from the plurality of luminaires defined as a combining distance. Additionally, the dominant source light wavelength of at least some of the luminaires of the plurality of luminaires may be variable with time. The plurality of luminaires may be configured to be operated to selectively emit light having a spectral power distribution that reduces melatonin suppression.

Each luminaire of the plurality of luminaires may further comprise a driver circuit and a plurality of light-emitting diodes (LEDs). The driver circuit may be configured to drive the plurality of LEDs with a ripple current at frequencies greater than about 200 Hz. Additionally, the spectral power distribution of the plurality of luminaires may have an associated maximum intensity at each wavelength. Furthermore, the plurality of luminaires are operable to emit 45% of the maximum intensity at a wavelength of 440 nm, 53% of the maximum intensity at a wavelength of 460 nm, 75% of the maximum intensity at a wavelength of 480 nm, 77% of the maximum intensity at a wavelength of 560 nm, 74% of the maximum intensity at a wavelength of 580 nm, and 71% of the maximum intensity at a wavelength of 600 nm.

In some embodiments, the driver circuit may be configured to control the intensity of light emitted by the respective luminaire through pulse-width modulation. Furthermore, the combined light may have a color temperature within the range from about 2,700 K to about 3,500 K.

Additionally, in some embodiments, the spectral power distribution of each luminaire of the plurality of luminaires may be alterable responsive to a time indicated by a time-keeping device in communication with the computerized device. At least one of the plurality of luminaires may be operable to emit light having at least one of increased spectral opponency and decreased spectral opponency responsive to the time indicated by the time-keeping device.

In some embodiments, at least one of the plurality of luminaires is operable to emit light having decreased spectral opponency to thereby increase melatonin suppression. The combined light is a white light. Furthermore, the combined light may comprise a plurality of wavelengths that are variable with time. The controller may operate the plurality of luminaires such that a selected wavelength of light is persistently included in the plurality of wavelengths. Additionally, a luminaire of the plurality of luminaires may be operable to emit a source light comprising two wavelengths. The source light may have a non-white color associated therewith.

In some embodiments, the combined light at the combining distance may have an area of illumination having a length and a width. The computerized device may be configurable to operate the plurality of luminaires so as to control a variation of at least one characteristic of the combined light along at least one of the length and the width of the area of illumination. Furthermore, the characteristic of the combined light controlled by the computerized device may be selected from the group consisting of color temperature, color rendering index, chromaticity, and luminous intensity. Additionally, the characteristic of the combined light controlled by the computerized device may not vary more than 5% across the length and width of the area of illumination.

Additionally, the computerized device may be configurable to determine the relative location of each luminaire of the plurality of luminaires with respect to an adjacent at least one luminaire of the plurality of luminaires and each other luminaire of the plurality of luminaires. In some embodiments, the computerized device may be configurable to receive a lighting scenario from a remote computerized device placed in electronic communication with the computerized device. The computerized device may further be configurable to operate the plurality of luminaires responsive to the lighting scenario received from the remote computerized device. Furthermore, the computerized device may be positioned in electronic communication with a network and configured to receive the lighting scenario from the remote computerized device across the network.

In some embodiments, each luminaire of the plurality of luminaires may be positioned at an offset distance from each other adjacent luminaire. The combining distance may be determined by the offset distance. Additionally, the combining distance may be less than a distance from the plurality of luminaires to about an eye level of an average observer.

DETAILED DESCRIPTION OF THE PREFERRED EMBODIMENT

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

An embodiment of the invention, as shown and described by the various figures and accompanying text, provides a lighting system for providing non-homogenous light. More specifically, a lighting system comprising a plurality of luminaires that that emit a plurality of source lights that combine to form a combined light at a distance from the plurality of luminaires is provided.

Figure 1:
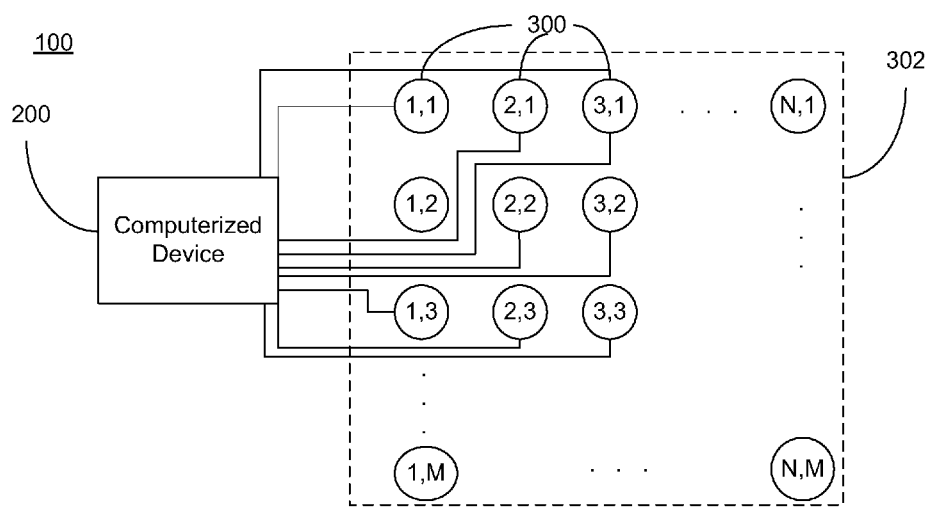
FIG. 1 is a schematic diagram of a lighting system according to an embodiment of the present invention.

Referring now to FIG. 1, a lighting system 100 will now be discussed in greater detail. The lighting system 100 may comprise a computerized device 200 and a plurality of luminaires 300. The computerized device 200 may be positioned in communication with each of the plurality of luminaires 300. Additionally, the computerized device 200 may be configured so as to individually operate each of the plurality of luminaires 300. The operation of the plurality of luminaires 300 by the computerized device 200 may cause some or all of the plurality of luminaires 300 to emit a source light. The source light emitted by each of the plurality of luminaires may propagate into a volume adjacent the plurality of luminaires 300 and combine to form a combined light. The plurality of luminaires 300 may be positioned in such a configuration so as to form an array of luminaires 302, as shown in FIG. 1. In some embodiments, the array 302 will be in a row-and-column configuration, such as an N by M array The computerized device 200 will now be discussed in greater detail. The computerized device 200 may be any electronic device that contains the necessary electronic components and attending circuitry to enable operation of the plurality of luminaires 300. For example, the computerized device 200 may include a microcontroller, such as an integrated circuit. Additionally, the computerized device 200 may include communication circuitry that enables the computerized device 200 to be positioned in communication with the plurality of luminaires 300. The communication between the computerized device 200 and the plurality of luminaires 300 may be accomplished by any electronic communication means or methods known in the art, including, but not limited to, Ethernet, Universal Serial Bus (USB), IEEE 1394/Firewire, ThunderBolt, 802.XX communication standards including WiFi, Bluetooth, ZigBee, RuBee, and all other wired and wireless communication standard known in the art. More details regarding communication between the computerized device 200 and the plurality of luminaires 300 may be found in U.S. patent application Ser. No. 13/403,531 titled Configurable Environmental Condition Sensing Luminaire, System and Associated Methods which is hereby incorporated by reference in its entirety.

Additionally, the computerized device 200 may include the necessary electronic components necessary to perform calculations to determine the characteristics of source light emitted by each of the plurality of luminaires 300 as well as the characteristics of a combined light comprising the source lights of all the plurality of luminaires 300 or, alternatively, a combined light comprising the source lights of a subset of the plurality of luminaires 300.

Moreover, the computerized device 200 may include electronic components that enable the communication device to communicate with another computerized device so as to receive a lighting scenario. A lighting scenario may be a picture, video, or other visual element that may be recreated, either in whole or in part, by the operation of the plurality of luminaires 300 by the computerized device 200. The receipt of a lighting scenario by the computerized device 200 may cause the computerized device 200 to operate the plurality of luminaires 300 responsive to the received lighting scenario. The computerized device 200 may communicate with the other computerized device so as to receive the lighting scenario by any means or method known in the art, including, but not limited to, the electronic communication means listed hereinabove. Moreover, the computerized device 200 may operate the plurality of luminaires 300 in a manner that varies with time responsive to the lighting scenario.

The lighting scenario may be a representation of an event. For example, the lighting scenario may be a representation of a naturally occurring phenomenon, such as, for example, the Aurora Borealis. As another example, the lighting scenario may be a representation of a human event, such as Mardi Gras. In any case, the lighting scenario is a visual representation of an event that has associated with it a varying visual element, usually including variations in color, brightness, and any other visual elements. These varying visual elements may be represented by the plurality of luminaires 300 through their operation by the computerized device 200. Accordingly, a person looking directly at the plurality of luminaires 300, such as when they are positioned in an array, may have the impression that they perceive the event that the lighting scenario represents. However, when not looking directly at the plurality of luminaires 300, but instead looking at the walls, floor, or any other object disposed within a volume within which the observer is positioned and into which the plurality of luminaires 300 are emitting light, the observer will not perceive the varying colors, brightness, or other characteristics of light that are varying in the light emitted by the plurality of luminaires 300 individually, as each of the individual emitted lights will have combined to form a light having generally consistent lighting characteristics, such as those that are generally associated with providing normal lighting to a room. More details regarding the combined light are provided hereinbelow.

The event that is being reproduced by the lighting scenario may be digitized in a number of ways. In some embodiments, a video capture device having a field of view may be positioned and operated so as to capture a video of the event. In some further embodiments, the video capture device may provide a video signal to the computerized device 200 in real-time such that the computerized device can recreate the event as it is happening. Such a configuration is typically accomplished by positioning in electrical communication each of the video capture device and the computerized device with a network, either directly or through connection to an intermediate electronic device. The video signal may then be sent from the video capture device to the computerized device 200 across the network. Often, a remote computerized device is used to facilitate communication between the video capture device and the computerized device 200. In some other embodiments, a person may use software to recreate the event artificially. In some other embodiments, an audio capture device may be positioned to receive audio input, either electronically or using a microphone, and transmit a signal to the computerized device that may present a visualization of the received audio input.

Additionally, the computerized device 200 may be associated with a memory within which a lighting scenario may be stored. The memory may be an integral part of the computerized device 200, or it may be temporarily attached to and associated with the computerized device 200. When the computerized device 200 receives a lighting scenario, the lighting scenario may be stored in the memory for retrieval at another time by the computerized device 200.

Where the plurality of luminaires 300 is formed into an array, the computerized device 200 may determine the location of each of the plurality of luminaires 300. More specifically, the computerized device 200 may determine the location of each luminaire 300 with respect to its adjacent luminaires 300, or it may determine the location of each luminaire 300 with respect to every other luminaire 300 of the plurality of luminaires 300. In order to determine the location of the plurality of luminaires 300, the computerized device 200 may enter an acquisition phase, wherein it transmits a signal to each of the plurality of luminaires 300. In some embodiments, the quantity and arrangement of the plurality of luminaires 300 may be predetermined, and a user may position the luminaires 300 accordingly. The signal sent by the computerized device 200 may either confirm the proper quantity and arrangement of the luminaires 300 or it may indicate a missing or an incorrectly arranged luminaire 300.

In some other embodiments, responsive to the locating signal sent from the computerized device 200, the luminaires 300 may operate a locating device comprised within either some or all of the luminaires 300 to determine their location. The locating device may function to determine the position of at least the containing luminaire 300 and potentially luminaires 300 adjacent thereto. The locating device may use any means or method in determining the above locations, including, without limitation, electromagnetic mapping, acoustic mapping, network trace mapping, visible light communication, radio communication, and any other method known in the art. These methods are exemplary only and do not limit the scope of the invention. The locating device may determine the location of the containing luminaire 300 either with respect to adjacent luminaires, with respect to the entire plurality of luminaires 300, with respect to the volume into which light emitted by the luminaire 300 will propagate, and any combination thereof. Moreover, the locating device may be configured to detect the presence of interfering objects within the volume or among the plurality of luminaires 300 that may affect the operation of the lighting system.

Once the locating device has determined the locations described above, it may transmit a response signal to the computerized device 200 providing location information for the containing luminaire 300, adjacent luminaires 300, the volume into which light emitted by the luminaire 300 will propagate, and any combination thereof. Once the computerized device 200 has received the response signal from each luminaire 300 containing a locating device, the computerized device may be programmed to determine how to operate the plurality of luminaires 300 to both represent the selected lighting scenario as well as to result in the selected combined light.

Figure 2:
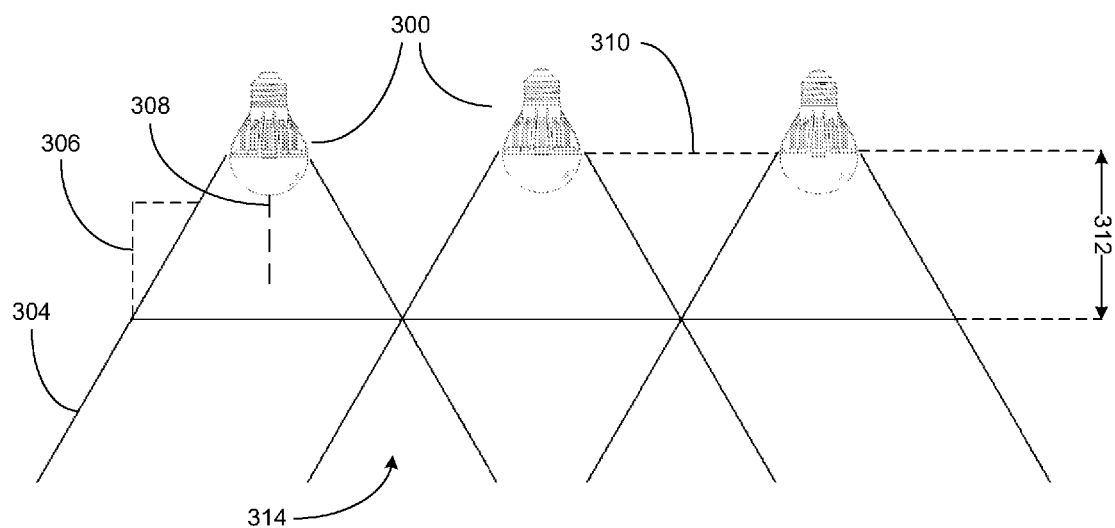
FIG. 2 is a side elevation view of a plurality of luminaires of a lighting system according to an embodiment of the present invention.

Referring now to FIG. 2, the plurality of luminaires 300 will now be discussed in greater detail. Each of the plurality of luminaires 300 may be configured to produce polychromatic light. Polychromatic light is light that comprises two or more wavelengths, hence being composed of two or more colors. More details regarding luminaires configured to produce polychromatic light, as well as the methods of producing polychromatic light generally, may be found in U.S. patent application Ser. No. 13/107,928 and U.S. Provisional Patent Application Ser. No. 61/643,308, both of which are incorporated by reference hereinabove. Some of the luminaires may be capable of generating a wider variety of lights, including having a broader color gamut, having greater or lesser color intensity, and the like.

As noted above, the computerized device 200 may selectively operate each of the plurality of luminaires 300. When a luminaire 300 is operated, it may emit a source light 304. The source light 304 of each luminaire 300 may have a known rate of lateral propagation 306. The rate of lateral propagation 306 may be described as the rate at which the source light 304 expands through a volume away from a longitudinal axis 308 of the source light 304. Each of the plurality of luminaires 300 may have an equivalent rate of lateral propagation 306, or some or all luminaires 300 may have a rate of lateral propagation 306 that is different from the other luminaires 300. Additionally, where the plurality of luminaires 300 are arranged to form an array 302, as depicted in FIG. 1, each pair of adjacent luminaires 300 may be separated by an offset distance 310. The proportion of the offset distance 310 to the rate of lateral propagation 306 of adjacent luminaires 300 may determine a combination distance 312. The combination distance 312 may be defined as a distance along the longitudinal axis 308 of a luminaire 300 where the source light 304 of a first luminaire 300 overlaps with the source light 304 of a second luminaire 300. In the present embodiment, the first and second luminaires 300 are adjacent to one another. Beyond the combination distance 312, the overlap between the source lights 304 of two or more luminaires 300 may be defined as a combined light 314. The offset distance 310, rate of lateral propagation 306, or both may be configured so as to result in a combination distance 312 that is generally less than the distance to the eye level of an average observer. Moreover, the offset distance 310 between each adjacent luminaires may be uniform, or it may vary. Moreover, the longitudinal axes 308 defined by each luminaire 300 may be parallel, intersecting, or skew. In further embodiments, some or all of the luminaires 300 may be capable of altering their offset distance 310 or angle of their longitudinal axis 308 by repositioning or rotating itself by any electrical, mechanical, magnet, or any other mechanism or system capable of enabling such movement. Moreover, such movement may be controlled by the computerized device 200 and the computerized device 200 may alter the source lights 304 of any moving luminaire 300 to compensate for such movement.

Additionally, in some embodiments, each luminaire of the plurality of luminaires 300 may be operable to emit light having an increased spectral opponency. It is understood in the art that certain wavelengths of light are associated with melatonin suppression in observers of light. More information regarding melatonin suppression may be found in U.S. patent application Ser. No. 13/652,207, which is incorporated by reference hereinabove in its entirety. Moreover, increasing spectral opponency, specifically opponency of generally blue light, is known to reduce melatonin suppression.

Therefore, in some embodiments, the computerized device 200 may be programmed to operate at least one of the plurality of luminaires 300 to emit light having a spectral power distribution that increases spectral opponency, thereby minimizing melatonin suppression. More specifically, the computerized device 200 may be programmed to operate the plurality of luminaires 300 to emit light having a spectral power distribution that reduces the intensity of light having a wavelength associated with melatonin suppression from a maximum intensity associated with that wavelength. For example, the computerized device 200 may operate at least one of the plurality of luminaires 300 to emit light having an intensity of not greater than about 45% of the maximum intensity at a wavelength of about 440 nm, an intensity of not greater than about 53% of the maximum intensity at a wavelength of about 460 nm, an intensity of not greater than about 75% of the maximum intensity at a wavelength of about 480 nm, an intensity of not greater than about 77% of the maximum intensity at a wavelength of about 560 nm, an intensity of not greater than about 74% of the maximum intensity at a wavelength of about 580 nm, and an intensity of not greater than about 71% of the maximum intensity at a wavelength of about 600 nm. The computerized device 200 may reduce the intensity of light at the above wavelengths through the use of any method known in the art, including, but not limited to, pulse-width modulation.

In some embodiments, the plurality of luminaires 300 may be configured to generate light through the use of light-emitting semiconductors, such as light-emitting diodes (LEDs). Where LEDs are employed, each luminaire of the plurality of luminaires 300 may further include a driver circuit configured to enable the operation of the LEDs by the computerized device 200. In some embodiments, the driver circuit may be configured to operate the LEDs with a ripple current at frequencies greater than 200 Hz. A ripple current at frequencies above 200 Hz is chosen to avoid biological effects that may be caused by ripple currents at frequencies below 200 Hz. For example, studies have shown that some individuals are sensitive to light flicker below 200 Hz, and in some instances experience headaches, seizures, etc.

Furthermore, in some embodiments, the computerized device 200 may be in communication with a time-keeping device. In some embodiments, the time-keeping device may be an atomic clock. The time-keeping device may generate an indication of the current time that is receivable by the computerized device 200. When the computerized device 200 receives the indication of time, it may operate the plurality of luminaires 300 responsive to the time indicated. For example, if the time indicated is generally associated with evening or night, the computerized device 200 may operate the plurality of luminaires 300 to emit light that generally does not suppress melatonin, therefore avoiding interfering with melatonin levels in observers. Alternatively, if it is desirous for melatonin to be suppressed, be it that the time indicated is generally in the morning or during the day, or if, for any other reason, it is desirous that melatonin be suppressed in an observer, the computerized device 200 may operate the plurality of luminaires to include light having decreased spectral opponency and to include light comprising wavelengths associated with melatonin suppression.

The combined light 314 may be a polychromatic light comprising the wavelengths of each of the source lights 304 that overlapped to form the combined light 314. In some embodiments, where the source lights 304 emitted by each of the plurality of luminaires 300 are monochromatic and have the same single wavelength, the resulting combined light 314 will be similarly monochromatic. In some other embodiments, where the source lights 304 each emit a polychromatic light, the polychromaticity of the combined light 314 will comprise an increased number of included wavelengths. As the wavelength of each source light 304 varies with time, so too will the wavelengths comprised by the combined light 314 vary with time.

Similar to the light emitted individually by each luminaire of the plurality of luminaires 300, the combined light 314 may have a spectral power distribution configured to increase spectral opponency to thereby reduce melatonin suppression. More specifically, the computerized device 200 may operate at least one of the plurality of luminaires 300 to emit light that, when combined to form the combined light 314, causes the spectral power distribution of the combined light 314 to have an intensity at wavelengths associated with melatonin suppression that is less than a maximum intensity. Yet more specifically, the computerized device 200 may operate the plurality of luminaires 300 such that the combined light 314 has an intensity of not greater than about 45% of the maximum intensity at a wavelength of about 440 nm, an intensity of not greater than about 53% of the maximum intensity at a wavelength of about 460 nm, an intensity of not greater than about 75% of the maximum intensity at a wavelength of about 480 nm, an intensity of not greater than about 77% of the maximum intensity at a wavelength of about 560 nm, an intensity of not greater than about 74% of the maximum intensity at a wavelength of about 580 nm, and an intensity of not greater than about 71% of the maximum intensity at a wavelength of about 600 nm.

Moreover, the combined light 314 may have other selected lighting characteristics, such as chromaticity, luminous intensity, color rendering index (CRI), color temperature, and any other lighting characteristic. For example, the combined light 314 may be a generally white light, may have luminous intensity within the range from about 100 lumens to about 2,600 lumens, may be a generally white light, may have a CRI of about 50 or greater, or may have a color temperature within the range from about 2,000 Kelvin to about 25,000 Kelvin, or any combination of the above. More specifically, where the color of the combined light 314 is selected, the combined light 314 may form a metamer, wherein the apparent color of the light is the result of the spectral power distribution of the combined source lights 304 combining to form the combined light 314. These selections of lighting characteristics are exemplary only and non-limiting and any other possible selection for each of the characteristics of light are contemplated and included within the scope of the invention.

As stated above, the computerized device 200 may control the operation of each of the plurality of luminaires 300. Furthermore, the computerized device 200 may be configured to operate each of the plurality of luminaires 300 to emit a source light 304 comprising one or more selected wavelengths.

The source light emitted by each luminaire 300 may include a dominant wavelength. The dominant wavelength may be within a range of wavelengths generally considered as within the visible spectrum of wavelengths. More specifically, the dominant wavelength may be within the range of from about 390 nanometers to about 750 nanometers. The dominant wavelength may principally define a color of the source light 304. The dominant wavelength may be a white color or a non-white color.

The color of the source light 304 of a luminaire 300 may be assigned to the luminaire 300 by the computerized device 200, which may operate the plurality of luminaires 300 according to a lighting scenario as described hereinabove. More specifically, the computerized device 200 may determine that a luminaire 300 will represent a portion of the lighting scenario, and operate that luminaire 300 so as to represent that portion of the lighting scenario, recreating the lighting characteristics of that portion of the lighting scenario, including such lighting characteristics such as luminous intensity, chromaticity, and any other characteristic which can be controlled by the operation of the luminaire 300.

Furthermore, the source light 304 emitted by each luminaire 300 may vary with time. More specifically, the computerized device 200 may operate a luminaire 300 to emit a first source light 304 having a first selected characteristic of light. After some interval of time, the computerized device 200 may operate the luminaire 300 to emit a second source light 304 having a second selected characteristic of light that differs from the first selected characteristic of light. Accordingly, the computerized device 200 may operate each of the plurality of luminaires 300 so as to vary the characteristics of the source lights 304 emitted thereby.

Figure 3:
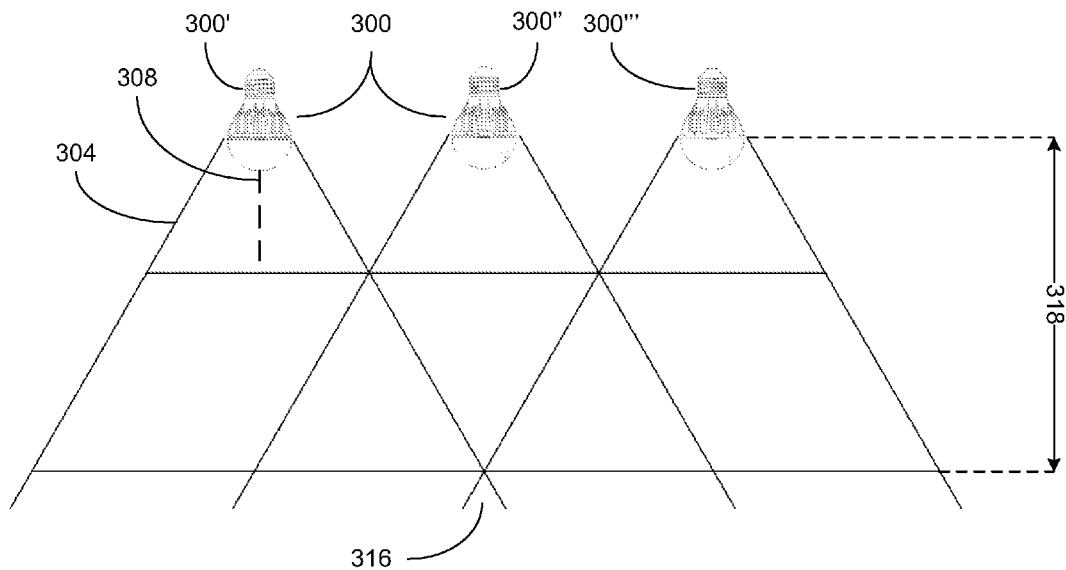
FIG. 3 is a side elevation view of a plurality of luminaires of a lighting system according to an embodiment of the present invention.

Turning now to FIG. 3, in some embodiments of the invention, the computerized device 200 may be configured to operate the plurality of luminaires 300 so as to emit source lights 304 that combine to form a second combined light 316 at a second combination distance 318 having desired lighting characteristics. The second combination distance 318 may be defined as a distance along the longitudinal axis 308 of a luminaire 300 where the source light 304 of a first luminaire 300' overlaps with the source light 304 of a second luminaire 300" and a third luminaire 300'". As such, the second combined light 316 may essentially contain within it the combined lights of each of the first luminaire 300' and the second luminaire 300" as well as the second luminaire 300" and the third luminaire 300'". Generally, the second combination distance 318 will be greater than a combination distance for the combined lights of the first luminaire 300' and the second luminaire 300" as well as the second luminaire 300" and the third luminaire 300'".

In each of the embodiments depicted in FIGS. 2 and 3, the combined lights 314, 316, will comprise one or more wavelengths that are determined by the source lights 304 emitted by each of the luminaires 300 that combine to form the combined lights 314, 316. Where the plurality of luminaires 300 comprises more than two luminaires in the case of combined light 314, and more than three luminaires 300 in the case of combined light 316, there will be more than one combined light formed in each of those embodiments. Accordingly, where the source lights 304 of a luminaire 300 comprises one or more wavelengths that differs from the source lights 304 of other luminaires 300, it is possible for there to be a variety of combined lights comprising different wavelengths in the polychromatic light. Accordingly, where the plurality of luminaires 300 are formed into an array, the combined light formed by the plurality of luminaires 300 may vary across the length and width of an area of illumination offset from the array at the combining distance, depending on what source lights 304 are combining to form the combined light at a given location.

Moreover, the computerized device 200 may control the operation to control the variation of the combined light formed by the plurality of luminaires 300 across the length and width of the area of illumination. More specifically, the computerized device 200 may control the operation of the plurality of luminaires 300 to control the variation of a characteristic of light, such as those disclosed hereinabove, of the combined light formed thereby. More specifically, the computerized device 200 may control the variation of the characteristic of light to not exceed 5% of a selected value or magnitude.

Figure 4:
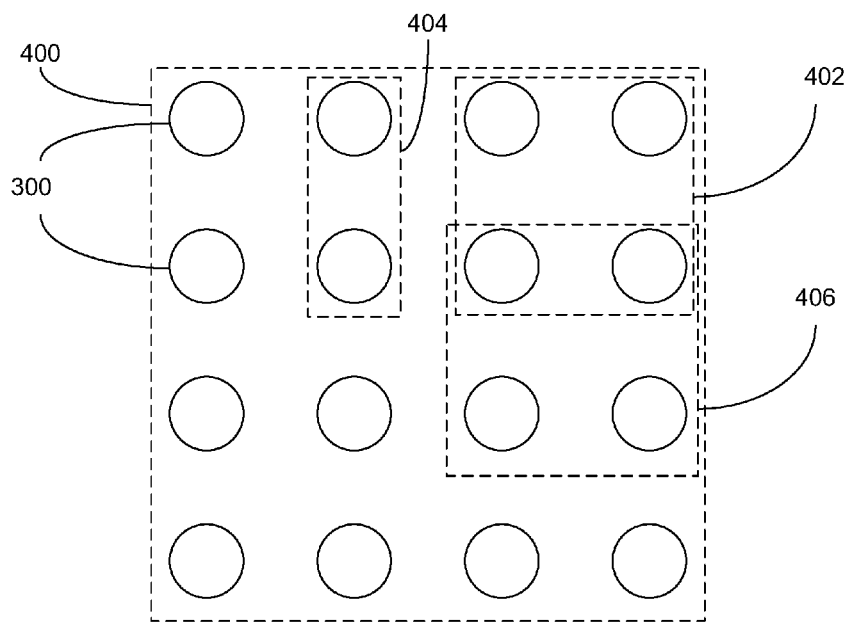
FIG. 4 is a bottom view of a lighting system according to an embodiment of the present invention.

In some embodiments, the lighting system may further comprise one or more optical sensors. The optical sensors may be positioned so as to measure the source lights, the combined lights, and reflections thereof throughout the volume through which they propagate. The optical sensors may be placed in electrical communication with the computerized device so as to function as a feedback system, providing information to the computerized device about the volume into which the light emitted by the luminaires is emitted, and if the desired combined light is being formed. Types of information included may be obstructions in the volume, the color of any walls or objects in the volume, the actual combined light, and the like. The computerized device may alter the source lights of the plurality of luminaires responsive to the indication of the characteristics of light being observed by the optical sensors.

Where the lighting system 100 forms two or more combined lights, in order to estimate what the combined lights of the lighting system 100 will be at a given location, the computerized device 200 may group subsets of the plurality of luminaires 300 into combination groups. Referring now to FIG. 4, an array 400 of luminaires 300 is depicted, wherein the luminaires 300 are positioned such that the array 400 is in a 4×4 grid configuration.

The computerized device 200 may determine a plurality of combination groups from the array 400 of luminaires 300. For instance, the computerized device 200 may designate a first combination group 402 comprising a four luminaires 300 in a 2×2 grid configuration. The computerized device 200 may operate each of the luminaires 300 of the first combination group such that a combined light formed by the first combination group 402 is a metamer comprising the wavelengths of light of each source light emitted by the luminaires 300. Moreover, the computerized device 200 may operate the luminaires 300 of the first combination group 402 such that the metamer formed thereby has one or more selected characteristic of light, such as those described hereinabove.

Similar to the combined light 304 as described hereinabove, the metamer may be configured to have a spectral power distribution that increases spectral opponency, thereby reducing melatonin suppression. More specifically, the computerized device 200 may operate at least one of the plurality of luminaires 300 to emit light that, when combined to form the metamer, causes the spectral power distribution of the metamer to have an intensity at wavelengths associated with melatonin suppression that is less than a maximum intensity. Yet more specifically, the computerized device 200 may operate the plurality of luminaires 300 such that the metamer has an intensity of not greater than about 45% of the maximum intensity at a wavelength of about 440 nm, an intensity of not greater than about 53% of the maximum intensity at a wavelength of about 460 nm, an intensity of not greater than about 75% of the maximum intensity at a wavelength of about 480 nm, an intensity of not greater than about 77% of the maximum intensity at a wavelength of about 560 nm, an intensity of not greater than about 74% of the maximum intensity at a wavelength of about 580 nm, and an intensity of not greater than about 71% of the maximum intensity at a wavelength of about 600 nm.

Still referring to FIG. 4, the computerized device may further designate a second combination group 404. The second combination group 404 may comprise two luminaires 300 positioned in a 1×2 array. The computerized device 200 may similarly operate the luminaires 300 of the second combination group 404 such that the metamer formed thereby has one or more selected characteristic of light. The characteristic of light selected for the metamer formed by the second combination group 404 may be the same as the selected characteristic of light for the metamer formed by the first combination group 402, or it may be different. Moreover, while the selected characteristics may be of the same type (i.e., chromaticity, luminous intensity, etc.), the magnitudes may be different. Moreover, due to the orientation of the luminaires 300 forming the second combination group 404, the combination height of the metamer formed thereby will be different from the combination height of the metamer formed by the first combination group 402.

Still referring to FIG. 4, the computerized device 200 may define a third combination group 406. The third combination group 406 may comprise four luminaires 300 positioned in a 2×2 array. Moreover, two of the luminaires 300 comprised by the third combination group 406 may also be included in the first combination group 402. Accordingly, the source lights emitted by luminaires 300 shared between the first combination group 402 and the third combination group 406 will be constituent components of the metamers formed by each of the combination groups. Moreover, any changes to those shared luminaires 300 will affect both metamers formed by the first and third combination groups 402, 406. This phenomenon will be discussed in greater detail hereinbelow.

Figure 5:
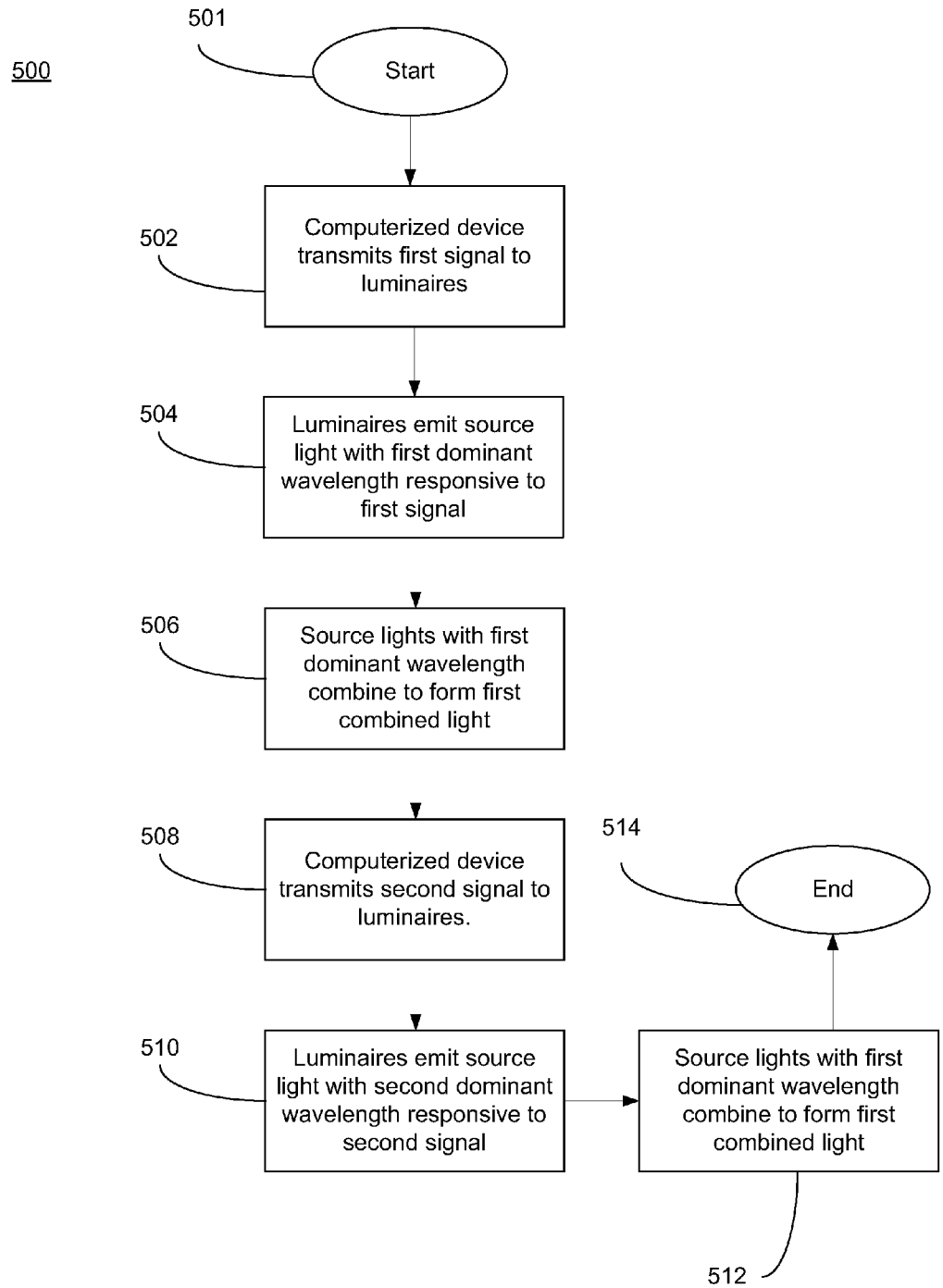
FIG. 5 is a flowchart illustrating a method of operating a lighting system according to an embodiment of the present invention.

Referring now to the flowchart 500 illustrated in FIG. 5, a method aspect of the present invention is now described in greater detail. The method according to the present invention, and as illustrated in the flowchart 500 of FIG. 5, is directed to a method of operating a lighting system to reproduce a lighting scenario while forming a combined light having selected characteristics of light. The lighting system may include some or all of the features described hereinabove.

From the Start (Step 501) a computerized device may send a first signal to a plurality of luminaires at Step 502. In some embodiments, the first signal may be configured to cause the plurality of luminaires to emit light having a spectral power distribution configured to increase spectral opponency, thereby reducing melatonin suppression, as described hereinabove. At Step 504 the luminaires may operate responsive to the first signal, emitting a source light having a first dominant wavelength. For at least two of the luminaires, the source light emitted by a first luminaire may have a different first dominant wavelength than a dominant wavelength of a source light for a second luminaire. At Step 506 the source lights emitted by the luminaires may combine to form a first combined light. At Step 508 the computerized device may transmit a second signal to the luminaires. The sequential nature of the above steps results in the second signal being transmitted at some time after the transmittal of the first signal. At Step 510 the luminaires may operate responsive to the second signal, emitting a source light having a second dominant wavelength. For at least one of the luminaires, the first dominant wavelength may be different than the second dominant wavelength. At Step 512 the source lights emitted by the luminaires having second dominant wavelengths may combine to form a second combined light. The method is ended at Step 514.

Figure 6:
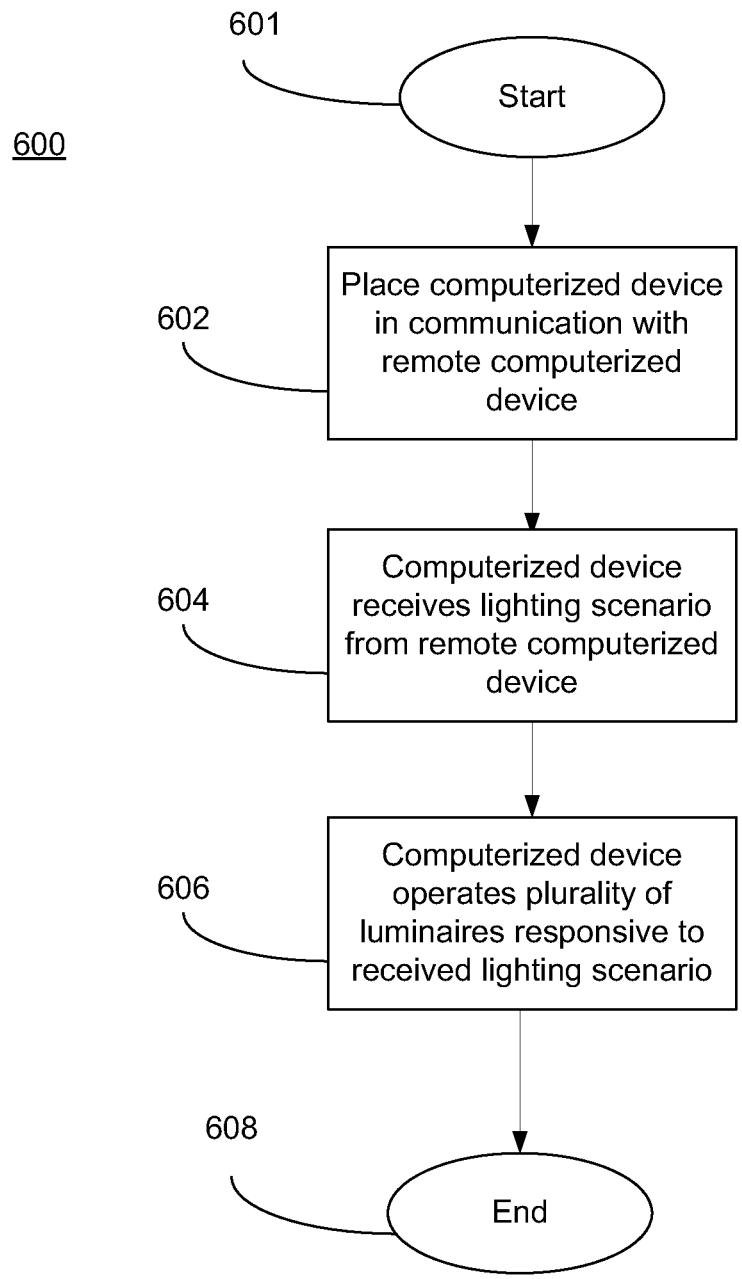
FIG. 6 is a flowchart illustrating a method of operating a lighting system according to an alternative embodiment of the present invention.

Referring now additionally to the flowchart 600 illustrated in FIG. 6, a method aspect of the present invention is now described in greater detail. The method according to the present invention, and as illustrated in the flowchart 600 of FIG. 6, is directed to a lighting system that operates responsive to a lighting scenario received from a remote computerized device. From the Start (Step 601) a computerized device of the lighting system may be placed in communication with a remote computerized device, as described hereinabove, at Step 602. At Step 604, the computerized device may receive from the remote computerized device a lighting scenario. As discussed hereinabove, the lighting scenario may be generated by a signal capture device, such as a video capture device, an audio capture device, a video playback device, an audio playback device, and the like. Furthermore, the lighting scenario may be captured live by the signal capture device. Alternatively, the lighting scenario may be pre-programmed on the remote computerized device. At Step 606, the computerized device may then operate a plurality of luminaires of the lighting system responsive to the received lighting scenario. For example, the computerized device may operate the luminaires as described in flowchart 500 as shown in FIG. 5. Any method of operation described in this application or known in the art are contemplated and included within the scope of the invention. The method is ended at Step 608.

Figure 7:
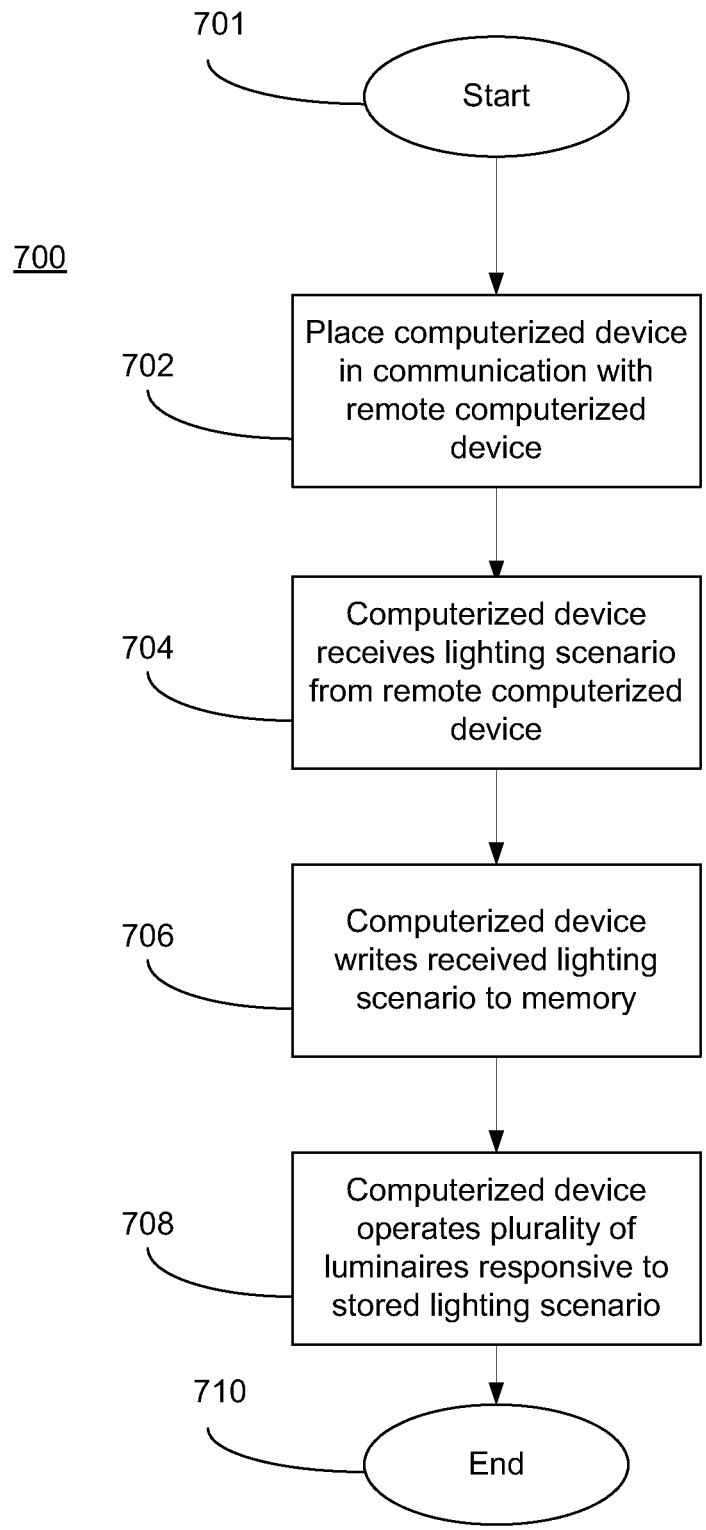
FIG. 7 is a flowchart illustrating a method of operating a lighting system according to an alternative embodiment of the present invention.

Referring now additionally to the flowchart 700 illustrated in FIG. 7, a method aspect of the present invention is now described in greater detail. The method according to the present invention, and as illustrated in the flowchart 700 of FIG. 7, is directed to a lighting system that includes a computerized device comprising a memory. From the Start (Step 701) a computerized device of the lighting system may be placed in communication with a remote computerized device, as described hereinabove, at Step 702. At Step 704 the computerized device may receive from the remote computerized device a lighting scenario, also as described hereinabove. At Step 706 the computerized device may write the received lighting scenario to a memory associated with the computerized device. At Step 708, the computerized device may retrieve the lighting scenario from the memory and operate the luminaires responsive to the stored lighting scenario, as described hereinabove. The method is ended at Step 710.

Figure 8:
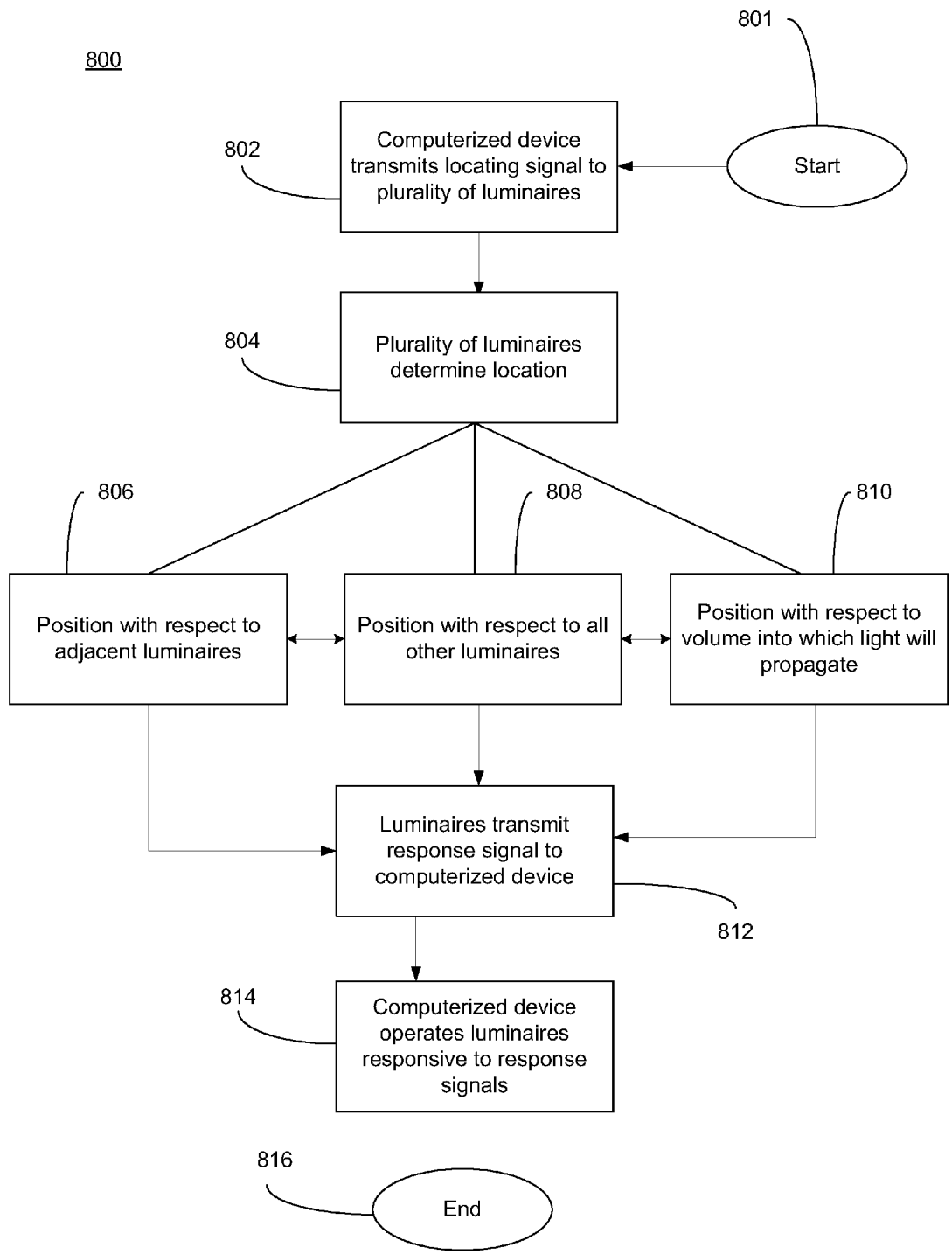
FIG. 8 is a flowchart illustrating a method of operating a lighting system according to an alternative embodiment of the present invention.

Referring now additionally to the flowchart 800 illustrated in FIG. 8, a method aspect of the present invention is now described in greater detail. The method according to the present invention, and as illustrated in the flowchart 800 of FIG. 8, is directed to a lighting system that determines the location of a plurality of luminaires positioned in an array. From the Start (Step 801) a computerized device may transmit a locating signal to each of a plurality of luminaires at Step 802. At Step 804 each of the plurality of luminaires may determine its location by any method disclosed hereinabove. Each luminaire may determine its location according to one of at least three location perspectives. Depending on the configuration and capabilities of a locating device included by at least some of the plurality of luminaires, the containing luminaires may determine its location with respect to at least one of its adjacent luminaires, as shown in Step 806, with respect to at least all the other luminaires of the plurality of luminaires, as shown in Step 808, or with respect to the volume into which light emitted by the plurality of luminaires will propagate into, as sown at Step 810, and any combination thereof. At Step 812 each luminaire may transmit a response signal to the computerized device providing its location information. At Step 814 the computerized device may operate the luminaires responsive to the response signals received from the luminaires. The location indicated by each response signal associated with each luminaire may facilitate the computerized device in determining which portion of the lighting scenario each luminaire may be assigned and operated to recreate. The method is ended at Step 816.

Figure 9:
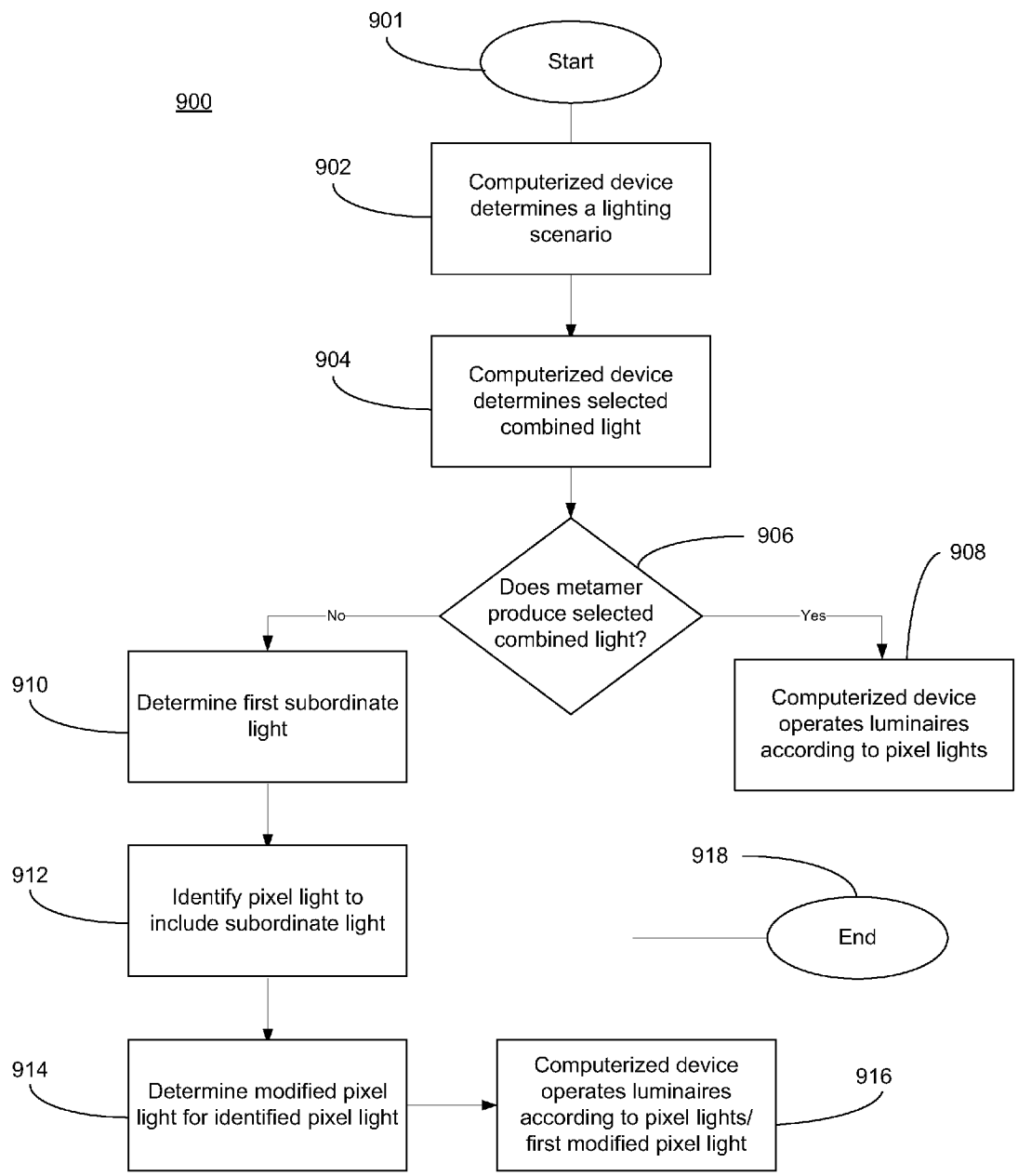
FIG. 9 is a flowchart illustrating a method of operating a lighting system according to an alternative embodiment of the present invention.

Referring now additionally to the flowchart 900 illustrated in FIG. 9, a method aspect of the present invention is now described in greater detail. The method according to the present invention, and as illustrated in the flowchart 900 of FIG. 9, is directed to a lighting system determines whether light emitted responsive to a lighting scenario will produce a selected combined light. From the Start (Step 901) a computerized device may determine a lighting scenario at Step 902. The determination of the lighting scenario may include the receipt of a lighting scenario as described hereinabove, or it may include the selection of one lighting scenario from many lighting scenarios available to the computerized device by any of the methods disclosed hereinabove. The lighting scenario of this embodiment may comprise a plurality of pixels arranged into an array. Furthermore, the determination of the lighting scenario may include assigning each pixel of the lighting scenario to a luminaire of the plurality of luminaires, defining a pixel light for each of the luminaires. The color of each pixel light may be designated a dominant wavelength of a source light for the luminaire associated with the pixel light.

In some embodiments, the lighting scenario may comprise a plurality of pixels that is greater in number than the number of luminaires in the plurality of luminaires. Alternatively, the lighting scenario may have an aspect ratio that is different than an aspect ratio of the array of luminaires. Accordingly, in determining the lighting scenario, the computerized device may render the lighting scenario either by pixelating, deresolving, cropping, resizing, or in some other way modifying the lighting scenario such that it may be producible by the plurality of luminaires.

At Step 904 the computerized device may determine a selected combined light. The selected combined light may be a combined light that has a selected characteristic of light as described hereinabove. The computerized device may determine the selected combined light by a number of methods. One such method is for the computerized device to be pre-programmed to include a predetermined combined light. Another method is for the computerized device to receive included with the lighting scenario a selected combined light. Another method is for the computerized device to receive an input providing the selected combined light. The input may be received from a variety of sources, including, without limitation, a remote computerized device, such as a computer terminal, a smart phone, a tablet computer, a wireless device specifically associated with the computerized device, or any other electrical device capable of transmitting the selected combined light to the computerized device. These methods and devices are exemplary only, and all possible methods and associated devices of providing the selected combined light to the computerized device are contemplated and included within the scope of the invention. Additionally, in some embodiments, the selected combined light may be configured to have a spectral power distribution configured to increase spectral opponency, thereby reducing melatonin suppression, as described hereinabove.

At Step 906 the computerized device may determine whether a metamer comprising the dominant wavelengths of the plurality of luminaires produces the selected combined light. If, at Step 906, it is determined the metamer comprising the dominant wavelengths of the plurality of luminaires will produce the selected combined light, then at Step 908 the computerized device may operate the plurality of luminaires according to each of their previously determined pixel lights.

However, if at Step 906 it is determined that the metamer comprising the dominant wavelengths of the plurality of luminaires does not produce the selected combined light, then at Step 910 the computerized device may determine a first subordinate light that, when combined with the metamer, will produce the selected combined light. At Step 912 the computerized device may identify a pixel light, and hence a luminaire, that can be adjusted to include the first subordinate light.

At Step 914 the computerized device may determine a modified pixel light that includes both the dominant wavelength for that pixel light as well as the first subordinate light. The computerized device may determine that, upon addition of the first subordinate light, the identified pixel light will still produce the color, luminous intensity, or other characteristic of light that is required for conformity with the lighting scenario. At Step 916 the computerized device may then operate the luminaires according to their pixel light or, in the case of the identified pixel light, the modified pixel light. The method is ended at Step 918.

Figure 10:
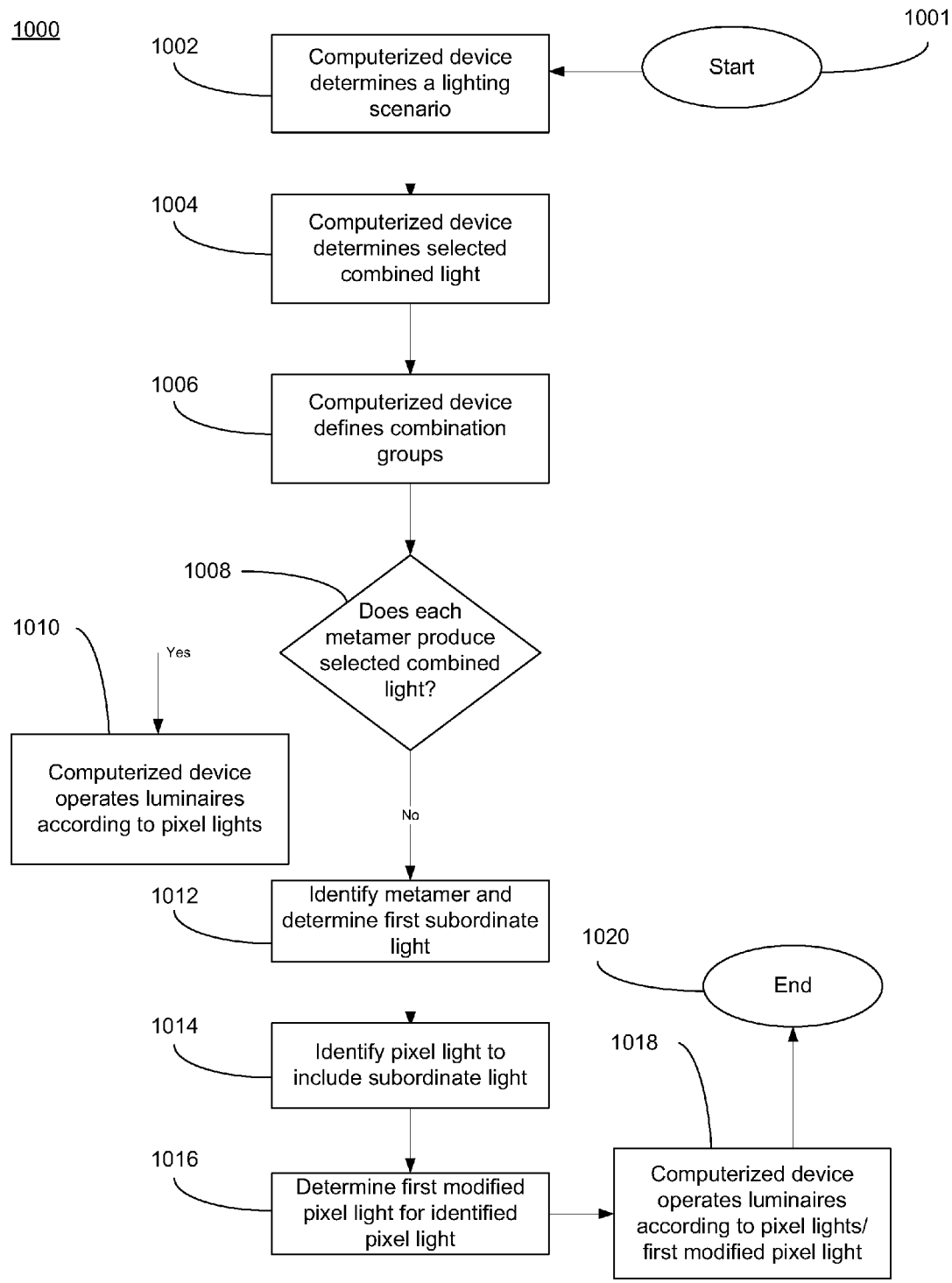
FIG. 10 is a flowchart illustrating a method of operating a lighting system according to an alternative embodiment of the present invention.

Referring now additionally to the flowchart 1000 illustrated in FIG. 10, a method aspect of the present invention is now described in greater detail. The method according to the present invention, and as illustrated in the flowchart 1000 of FIG. 10, is directed to a lighting system similar to that described in flowchart 900 of FIG. 9 wherein the computerized device determines a plurality of metamers.

From the Start (Step 1001) the computerized device may determine a lighting scenario, as described hereinabove, at Step 1002. At Step 1004 the computerized device may determine the selected combined light as described hereinabove. At Step 1006 the computerized device may define a plurality of combination groups consisting of subsets of the plurality of luminaires. The various configurations of combination groups are disclosed hereinabove. Each combination group defined by the computerized device has associated with it a metamer comprising the dominant wavelengths of each of the pixel lights of the combination groups.

At Step 1008 the computerized device may determine whether the metamers of each combination group produces the selected combined light. If, at Step 1008, it is determined the metamer comprising the dominant wavelengths of the plurality of luminaires will produce the selected combined light, then at Step 1010 the computerized device may operate the plurality of luminaires according to each of their previously determined pixel lights.

However, if at Step 1008 it is determined that one or more of the metamers does not produce the selected combined light, then at Step 1012 the computerized device may identify the non-conforming metamer and determine a first subordinate light that, when combined with the metamer, will produce the selected combined light. At Step 1014 the computerized device may identify a first pixel light selected from the pixel lights of the non-conforming combination group that can be adjusted to include the first subordinate light.

At Step 1016 the computerized device may determine a first modified pixel light that includes both the dominant wavelength for the identified pixel light as well as the first subordinate light. The computerized device may determine that, upon addition of the first subordinate light, the identified pixel light will still produce the color, luminous intensity, or other characteristic of light that is required for conformity with the lighting scenario. At Step 1018 the computerized device may then operate the luminaires according to their pixel light or, in the case of the identified pixel light, the modified pixel light.

It is contemplated that more than one combination group may produce a metamer that does not produce the selected combined light. Steps 1012, 1014, and 1016 may be repeated for each combination group producing a non-conforming metamer. The method is ended at Step 1020.

Figure 11:
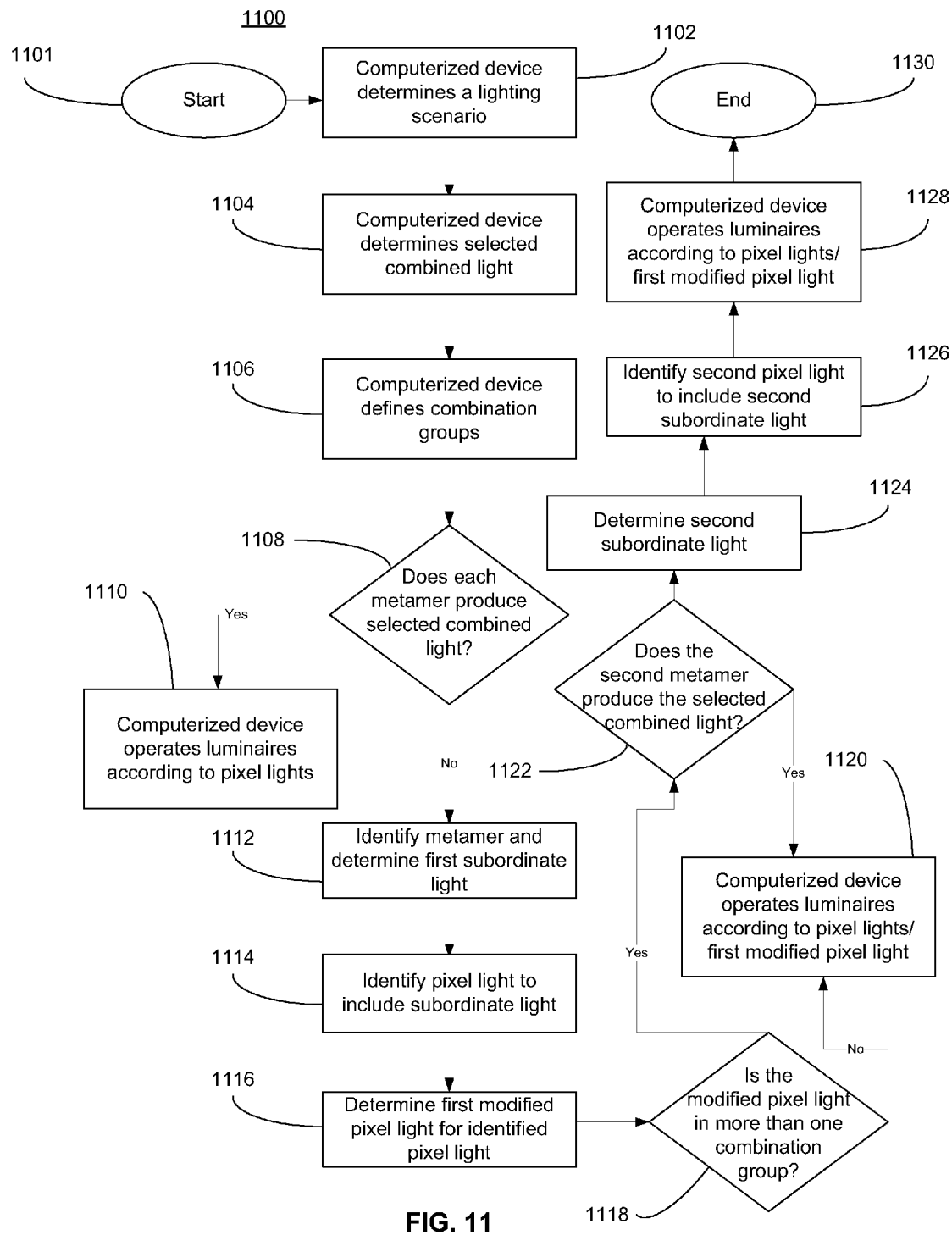
FIG. 11 is a flowchart illustrating a method of operating a lighting system according to an alternative embodiment of the present invention.

Referring now additionally to the flowchart 1100 illustrated in FIG. 11, a method aspect of the present invention is now described in greater detail. The method according to the present invention, and as illustrated in the flowchart 1100 of FIG. 11, is directed to a lighting system similar to that described in flowchart 1000 of FIG. 10 wherein the computerized device determines a plurality of metamers, further wherein the computerized device defines a plurality of combination groups that are overlapping, such that one luminaire may be included in two or more combination groups.

From the Start (Step 1101) the computerized device may determine a lighting scenario, as described hereinabove, at Step 1102. At Step 1104 the computerized device may determine the selected combined light as described hereinabove. At Step 1106 the computerized device may define a plurality of combination groups consisting of subsets of the plurality of luminaires as described hereinabove. At Step 1108 the computerized device may determine whether the metamers of each combination group produces the selected combined light. If, at Step 1108, it is determined the metamer comprising the dominant wavelengths of the plurality of luminaires will produce the selected combined light, then at Step 1110 the computerized device may operate the plurality of luminaires according to each of their previously determined pixel lights.

However, if at Step 1108 it is determined that one or more of the metamers does not produce the selected combined light, then at Step 1112 the computerized device may identify the non-conforming metamer and determine a first subordinate light that, when combined with the metamer, will produce the selected combined light. At Step 1114 the computerized device may identify a first pixel light selected from the pixel lights of the non-conforming combination group that can be adjusted to include the first subordinate light.

At Step 1116 the computerized device may determine a first modified pixel light that includes both the dominant wavelength for the identified pixel light as well as the first subordinate light. The computerized device may determine that, upon addition of the first subordinate light, the identified pixel light will still produce the color, luminous intensity, or other characteristic of light that is required for conformity with the lighting scenario.

As stated above, the combination groups of this embodiment may overlap such that one luminaire may be included in two or more combination groups. Accordingly, when a modified pixel light is determined, it is possible that the modified pixel light may be associated with a luminaire that is included in more than one combination group, namely a first and second combination groups, wherein at least the first combination group is determined to be producing a non-conforming metamer. Moreover, should that luminaire be included in more than one combination group, it is possible that while the modified pixel light may cause the previously non-conforming metamer of the first combination group to produce the selected combined light, it may have the unintended consequence of causing the metamer of the second combination group to become non-conforming. Accordingly, at Step 1118, the computerized device may determine whether the modified pixel light is included in more than one combination group. If it is determined that the modified pixel light is not associated with more than one combination group, then at Step 1120 the computerized device may then operate the luminaires according to their pixel light or, in the case of the identified pixel light, the modified pixel light.

However, if at Step 1118 it is determined the modified pixel light is included in more than one combination group, then at Step 1122 the computerized device may determine whether a second metamer associated with a second combination group now including the modified pixel light produces the selected combined light. If the second metamer produces the selected combined light, then the method may proceed to Step 1120 and the computerized device may operate the luminaires according to their pixel light or, in the case of the identified pixel light, the modified pixel light.

However, if at Step 1122 it is determined that the second metamer does not produce the second combined light, then at Step 1124 the computerized device may determine a second subordinate light that, when combined with the second metamer, produces the selected combined light. At Step 1126 the computerized device may then identify a second pixel light from the pixel lights included in the second combination group to include the second subordinate light. The second identified pixel light may be the same as the first identified pixel light, or it may be a pixel light of the second combination group other than the first identified pixel light.

At Step 1128 the computerized device may determine a second modified pixel light that includes both the dominant wavelength for the second identified pixel light as well as the second subordinate light. The computerized device may determine that, upon addition of the second subordinate light, the second identified pixel light will still produce the color, luminous intensity, or other characteristic of light that is required for conformity with the lighting scenario.

It is appreciated that Step 1118 may be performed for the second modified pixel light, with Steps 1120 through 1126 potentially being performed again. It is contemplated that these steps may be performed iteratively until it is determined by the computerized device that the metamer of every combination group produces the selected combined light. Accordingly, the computerized device may operate the luminaires according to their respective pixel light, first modified pixel light, second modified pixel light, and any number modified pixel light as is required. The method is ended at Step 1130.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

What is claimed is:

1. A lighting apparatus comprising:
a plurality of luminaires, each luminaire comprising a controller configured to operate the luminaire and positioned in communication with a computerized device;
wherein each luminaire is selectively operable to emit source light, the source light is characterized by a dominant source light wavelength within a range from 390 nanometers to 750 nanometers;
wherein the plurality of luminaires are arrangeable so as to form an array;
wherein at least some luminaires of the plurality of luminaires are operable such that at least two of the plurality of luminaires emit source lights with different dominant source light wavelengths, and such that the one or more source lights emitted by the plurality of luminaires combine to form a combined light at a distance from the plurality of luminaires defined as a combining distance;
wherein the dominant source light wavelength of at least some of the luminaires of the plurality of luminaires are variable with time;
wherein the plurality of luminaires are configured to be operated to selectively emit light having a spectral power distribution that reduces melatonin suppression;
wherein at least one of the plurality of luminaires is operable to emit light having at least one of increased spectral opponency and decreased spectral opponency responsive to a time indicated by a time-keeping device in communication with the computerized device.

2. The lighting apparatus according to claim 1 wherein each luminaire of the plurality of luminaires comprises a driver circuit and a plurality of light-emitting diodes (LEDs).

3. The lighting apparatus according to claim 2 wherein the driver circuit is configured to drive the plurality of LEDs with a ripple current at frequencies greater than 200 Hz.

4. The lighting apparatus according to claim 2 wherein the spectral power distribution of the plurality of luminaires has an associated maximum intensity at each wavelength; wherein the plurality of luminaires are operable to emit 45% of the maximum intensity at a wavelength of 440 nm, 53% of the maximum intensity at a wavelength of 460 nm, 75% of the maximum intensity at a wavelength of 480 nm, 77% of the maximum intensity at a wavelength of 560 nm, 74% of the maximum intensity at a wavelength of 580 nm, and 71% of the maximum intensity at a wavelength of 600 nm.

5. The lighting apparatus according to claim 4 wherein the driver circuit is configured to control the intensity of light emitted by the respective luminaire through pulse-width modulation.

6. The lighting apparatus according to claim 1 wherein the combined light has a color temperature within the range from 2,700 K to 3,500 K.

7. The lighting apparatus according to claim 1 wherein at least one of the plurality of luminaires is operable to emit light having decreased spectral opponency to thereby increase melatonin suppression.

8. The lighting apparatus according to claim 1 wherein the combined light is a white light.

9. A lighting apparatus according to claim 1 wherein the combined light comprises a plurality of wavelengths that are variable with time.

10. A lighting apparatus according to claim 1 wherein the controller operates the plurality of luminaires such that a selected wavelength of light is persistently included in the plurality of wavelengths.

11. A lighting apparatus according to claim 1 wherein a luminaire of the plurality of luminaires is operable to emit a source light comprising two wavelengths; and wherein the source light has a non-white color associated therewith.

12. A lighting apparatus comprising:
a computerized device; and
a plurality of luminaires, each luminaire comprising a controller configured to operate the luminaire and positioned in communication with the computerized device;
wherein each luminaire is selectively operable to emit source light, each source light having a dominant source light wavelength within a range from 390 nanometers to 750 nanometers;
wherein the plurality of luminaires are arrangeable so as to form an array;
wherein the computerized device is programmable to operate at least some luminaires of the plurality of luminaires such that at least two of the plurality of luminaires emit source lights with different dominant source light wavelengths, and such that one or more source lights emitted by the plurality of luminaires combine to form a combined light at a distance from the plurality of luminaires defined as a combining distance;
wherein the computerized device is configurable to vary the dominant source light wavelength of at least some luminaires of the plurality of luminaires with time; and
wherein the plurality of luminaires are configured to be operated to selectively emit light having a spectral power distribution that reduces melatonin suppression.

13. A lighting apparatus according to claim 12 wherein the combined light is a white light.

14. A lighting apparatus according to claim 12 wherein the combined light at the combining distance has an area of illumination having a length and a width; and wherein the computerized device is configurable to operate the plurality of luminaires so as to control a variation of at least one characteristic of the combined light along at least one of the length and the width of the area of illumination.

15. A lighting apparatus according to claim 14 wherein the characteristic of the combined light controlled by the computerized device is selected from the group consisting of color temperature, color rendering index, chromaticity, and luminous intensity.

16. A lighting apparatus according to claim 14 wherein the characteristic of the combined light controlled by the computerized device does not vary more than 5% across the length and width of the area of illumination.

17. A lighting apparatus according to claim 12 wherein the combined light comprises a plurality of wavelengths that are variable with time.

18. A lighting apparatus according to claim 17 wherein the controller operates the plurality of luminaires such that a selected wavelength of light is persistently included in the plurality of wavelengths.

19. A lighting apparatus according to claim 12 wherein a luminaire of the plurality of luminaires is operable to emit a source light comprising two wavelengths; and wherein the source light has a color associated therewith that is non-white.

20. A lighting apparatus according to claim 12 wherein the computerized device is configurable to determine the relative location of each luminaire of the plurality of luminaires with respect to an adjacent at least one luminaire of the plurality of luminaires and each other luminaire of the plurality of luminaires.

21. A lighting apparatus according to claim 12 wherein the computerized device is configurable to receive a lighting scenario from a remote computerized device placed in electronic communication with the computerized device; and wherein the computerized device is configurable to operate the plurality of luminaires responsive to the lighting scenario received from the remote computerized device.

22. A lighting apparatus according to claim 21 wherein the computerized device is positioned in electronic communication with a network; and wherein the computerized device is configured to receive the lighting scenario from the remote computerized device across the network.

23. A lighting apparatus according to claim 12 wherein each luminaire of the plurality of luminaires is positioned at an offset distance from each other adjacent luminaire; and wherein the combining distance is determined by the offset distance.

24. A lighting apparatus according to claim 12 wherein the combining distance is less than a distance from the plurality of luminaires to an eye level of an average observer.

* * * * *